(12) United States Patent
Bydder et al.

(10) Patent No.: US 7,474,097 B2
(45) Date of Patent: Jan. 6, 2009

(54) MAGNETIC RESONANCE IMAGING WITH ULTRA SHORT ECHO TIMES

(75) Inventors: Mark Bydder, San Diego, CA (US); Graeme M. Bydder, San Diego, CA (US); Matthew Robson, Oxford (GB); Peter Gatehouse, London (GB)

(73) Assignee: The Regents of the University of California, Oakland, CA (US)

( * ) Notice: Subject to any disclaimer, the term of this patent is extended or adjusted under 35 U.S.C. 154(b) by 130 days.

(21) Appl. No.: 10/571,039

(22) PCT Filed: Sep. 8, 2004

(86) PCT No.: PCT/US2004/029507

§ 371 (c)(1),
(2), (4) Date: Nov. 6, 2006

(87) PCT Pub. No.: WO2005/026748

PCT Pub. Date: Mar. 24, 2005

(65) Prior Publication Data

US 2007/0080685 A1 Apr. 12, 2007

Related U.S. Application Data

(60) Provisional application No. 60/501,451, filed on Sep. 8, 2003.

(51) Int. Cl.
G01V 3/00 (2006.01)
(52) U.S. Cl. .................... 324/307; 324/309
(58) Field of Classification Search ............ 324/307, 324/309
See application file for complete search history.

(56) References Cited

U.S. PATENT DOCUMENTS

| 5,025,216 A | 6/1991 | Pauly et al. |
| 5,150,053 A | 9/1992 | Pauly et al. |
| 5,510,713 A | 4/1996 | Bernstein |
| 6,016,057 A | 1/2000 | Ma |
| 6,304,084 B1 | 10/2001 | Star-Lack et al. |
| 6,583,623 B1 | 6/2003 | Kwok et al. |
| 2006/0214659 A1* | 9/2006 | Larson et al. ............. 324/307 |
| 2007/0255129 A1* | 11/2007 | Du et al. .................. 600/410 |

OTHER PUBLICATIONS

Benjamin M, Ralphs JR. Fibrocartilage in tendons and ligaments—an adaptation to compressive load. *J Anat* 1998; 481-494.
Bergin CJ, Noll DC, Pauly JM, Glover GH, Macovski A. MR imaging of lung parenchyma: a solution to susceptibility. *Radiology* 1992; 183: 673-676.
Bergin CJ, Pauly JM, Macovski A. Lung parenchyma: projection reconstruction MR imaging. *Radiology* 1991: 179: 771-781.
Brossman J, Frank LR, Pauly JM, et al. Short echo time projection reconstruction MR imaging of cartilage with histopathologic correlation: comparison with fat-suppressed spoiled Grass and magnetization transfer contrast MR imaging. *Radiology* 1997; 203: 501-507.

(Continued)

*Primary Examiner*—Louis M Arana
(74) *Attorney, Agent, or Firm*—Fish & Richardson P.C.

(57) ABSTRACT

Systems and techniques for imagining samples including components with small values of $T_2$. Optionally, the systems and techniques may provide (for example) suppression of unwanted signals, enhanced contrast, and artifact control in imaging samples with small values of $T_2$.

34 Claims, 28 Drawing Sheets

OTHER PUBLICATIONS

Chappell KE, Gatehouse PD, Williams AD, et al. Clinical imaging of the liver with ultrashort TE pulse sequences. *Proc Int Soc Magn Reson Med* 2003. Toronto, Canada. (1 page).

Chappell, K., et al., "Magnetic Resonance Imaging of the Liver With Ultrashort TE (UTE) Pulse Sequences" *Journal of Magnetic Resonance Imaging* 18:709-713 (2003). Published online in Wiley InterScience [<URL:http://www.interscience.wiley.com>].

Edelstein WA, Bottomley PA, Hart HR, Leue WM, Schenck JF, Redington RW. (in) ) RL Witcofski, N Karstaedt, CL Partain (eds). NMR Imaging. Bowman Gray School of Medicine, Winston Salem 1982. p. 139-146.

Fenrich FR, Beaulieu C, Allen PS. Relaxation times and microstructures. *NMR Biomed*. 2001; 14:133-9.

Frank LR, Wong EC, Buxton RB, Resnick D. Mapping the physiological parameters of articular cartilage with magnetic resonance imaging. *Top Magn Reson Imag* 1999; 10: 153-179. Published by Lippincott Williams & Wilkins, Inc., Philadelphia, PA, USA.

Gatehouse PD, Bydder GM. Magnetic resonance imaging of short $T_2$ components in tissues. *Clin Radiol* 2003; 58: 1-19. Published by Elsevier Science Ltd., [Available online at <URL:http//www.sciencedirect.com>].

Gatehouse PD, Thomas RW, Karadaglis D, et al. Imaging of the knee with ultrashort TE (UTE) pulse sequences. *Proc Int Soc Magn Reson Med* 2003. Toronto, Canada. (1 page).

Gatehouse PD, Waldman A, Van Dellen JR, et al. Clinical imaging of the brain with ultrashort TE (UTE) pulse sequences. *Proc Int Soc Magn Reson Med* 2003. Toronto, Canada. (1 page).

Gatehouse, P., et al., "Contrast-enhanced MRI of the menisci of the knee using ultrashort echo time (UTE) pulse sequences: imaging of the red and white zones" *The British Journal of Radiology*, 77 (2004), 641-647. Published by The British Institute of Radiology, UK.

Gatehouse, P., et al., "MR imaging of degenerative disc disease in the lumbar spine with ultrashort TE pulse sequences" MAGMA Magn Reson Mater Phy (2004) 16:160-166. [Published online Feb. 20, 2004.] Published by Springer Berlin / Heidelberg [Abstract available on the Internet at <URL:http://www.springerlink.com/content/61j65ed7evev216w/?p=4f4c5f77f7d841258584d5c781ed9a18&pi=1>.

Gold G, Pauly J, Moretto J, Glover G, Macovski A, Herfkens R. Characterization of artherosclerotic plaque at 1.5T. *J Magn Reson Imaging* 1993; 3: 399-407. Published by the Society for Magnetic Resonance Imaging Berkely, CA, USA.

Gold GE, Pauly JM, Leung AN, et al. Short echo time MR spectroscopic imaging of the lung parenchyma. *J Magn Reson Imaging* 2002; 15: 679-684. Published online in Wiley InterScience. [Available on the Internet at <URL:http://www.interscience.wiley.com>].

Gold GE, Pauly JM, Macovski A, Herfkens RJ. MR spectroscopic imaging of collagen: tendons and knee menisci. *Magn Reson Med* 1995; 34: 674-54. [Published by Williams & Wilkins, Baltimore, MD, USA].

Gold GE, Wren Tal, Nayak KS. In vivo short echo time imaging of Achilles Tendon. *Proc Int Soc of Magn Reson Med* 2001; p. 244. [Presented Apr. 21-27, 2001, Glasgow, Scotland, UK].

Gold GE. Thedens DR, Pauly JM, et al. MR imaging of the articular cartilage of the knee: new methods using ultrashort TE's. *Am J Roentgenol AJR* 1998; 170: 1223-1226. [Presented at the annual meeting of the American Roentgen Ray Society, Boston, May 1997.].

Hall-Craggs, M., "Ultrashort echo time (UTE) MRI of the spine in thalassaemia" *The British Journal of Radiology*, 77(2004), pp. 104-110. Published by the British Institute of Radiology, UK.

Harrison R, Bronskill MJ, Henkelman RM. Magnetization transfer and $T_2$ relaxation components in tissue. *Magn Reson Med* 1995; 33: 490-496. Published by Williams & Wilkins, Baltimore, MD, USA.

Hauger O, Frank LR, Boutin RD, et al. Characterization of the "red zone" on knee meniscus: MR imaging and histologic correlation. *Radiology* 2000; 217: 1293-200. [Published on the Internet at URL:http://radiology.rsnajnls.org/cgi/reprint/217/1/193?maxtoshow=&HITS=10&hits=10&RESULTFORMAT=&author1=hauger&fulltext=knee&searchid=1&FIRSTINDEX=0&sortspec=relevance&resourcetype=HWCIT>].

Hayes CW, Parellada JA. The magic angle effect in musculoskeletal MR imaging. *Top Magn Reson Imaging* 1996; 8: 51-56. Published by Lippincott-Reven Publishers, Philadelphia, PA, USA.

Henkelman RM, Stanisz GJ, Graham GJ. Magnetization transfer in MRI: a review. *NMR Biomed* 2001; 14: 57-64. Published by John Wiley & Sons, Ltd.

Henkelman RM, Stanisz GJ, Kim JK, Bronskill MJ. Anisotropy of NMR properties of tissue. *Magn Reson Med* 1994; 32: 592-602. Published by Williams & Wilkins, Baltimore, MD, USA.

Joy, M., "MRI—K-Space," Jan. 2003 [Retrieved from the Internet Jun. 17, 2008], [Available on the Internet at <URL:http://www.ecf.utoronto.ca/apsc/courses/bme595f/notes/MRI/kspace6.pdf>].

Lu A, Grist TG, Black WF. Improved spectral selectivity and reduced susceptibility in true-FISP using a near zero TE undersampled 3D PR sequence. *Proc Int Soc Magn Reson Med*. 10 (2002) p. 470 (1 page.).

Nayak KS, Pauly JM, Gold GE, Nishimura DG. Imaging ultrashort $T_2$ species in the brain. *Proc Int Soc Magn Reson Med* 2000; p. 509, Denver Colorado, USA Apr. 1-7, 2000.

Neilson HT, Gold GE, Olcott EW, Pauly JM, Nishimura DG. Ultrashort echo time 2D time of flight MR angiography using a half-pulse excitation. *Magn Reson Med* 1999; 41: 5921-599.

Oatridge A, Herlihy A, Thomas RW, et al. Magic angle imaging of the Achilles tendon in patients with chronic tendonopathy. *Clin Radiol* 2003; 58: 384-388. Published by Elsevier Science Ltd.

Oatridge A, Herlihy AH, Thomas RW, et al. Magnetic resonance: magic angle imaging of the Achilles tendon. *Lancet* 2001; 358-1610-11. Published by Elsevier Science Ltd.

Ouwerkerk R, Bleich KB, Gitten JS, Pomper MG, Bottomley PA. Tissue sodium concentration in human brain tumours as measured with $^{23}$Na MR imaging. *Radiology* 2003; 227: 529-537. [Published on the Internet before print on Mar. 27, 2003]<URL:http://radiology.rsnajnls.org/cgi/content/full/227/2/529?maxtoshow=&HITS=10&hits=10&RESULTFORMAT=&author1=ouwerkerk&fulltext&tissue&search=1&FIRSTINDEX=0&sortspec=relevance&resourcetype=HWCIT>.

Pauly J, Conolly S, Macovski A. Suppression of long $T_2$ components for short $T_2$ imaging. *J Magn Reson Imag* 1992; 2(P):145. Published by the Society for Magnetic Resonance Imaging, Berkely, CA, USA.

Pruessmann KP, Weiger M, Bornert P, Boesinger P. Advances in sensitivity encoding with arbitrary k-space trajectories. *Magn Reson Med* 2001; 46: 638-51.

Reichert IHL, Gatehouse PD, Firmin DN, et al. Proton imaging of periosteum and cortical bone with ultrashort TE pulse sequences, *Proc Int Soc Magn Reson Med* 2003. Toronto, Canada. (2 pages).

Reichert, I., et al., "Magnetic Resonance Imaging of Periosteum With Ultrashort TE Pulse Sequences" *Journal of Magnetic Resonance Imaging* vol. 19 (11 pages) [Published online in Wiley InterScience]<URL:http:www.interscience.wiley.com>.

Robson MD, Gatehouse PD, He T, Firmin DN, Bydder GM, Neubauer S. Human in-vivo imaging of phosphorus in cortical bone using ultrashort TE pulse sequences. *Proc Int Soc Magn Reson Med* 2003 (1 page).

Robson et al., "Contrast enhancement of short T2 tissues using ultrashort TE (UTE) pulse sequences" *Clinical Radiology* (2004) 59, 720-726. Published by Elsevier Ltd.

Robson, et al., " Human Imaging of Phosphorus in Cortical and Trabecular Bone In Vivo" *Magnetic Resonance in Medicine* 51:888-892 (2004) [Published online in Wiley InterScience] <URL:http://www.interscience.wiley.com>.

Robson, et al., "Magnetic resonance imaging of the Achilles tendon using ultrashort (UTE) pulse sequences" *Clinical Radiology* (2004) 59, 727-735. Published by Elsevier Ltd.

Robson, M. D., "Magnetic Resonance: An Introduction to Ultrashort TE (UTE) Imaging," *Journal of Computer Assisted Tomography*, 27(6):825-846 (Nov./Dec. 2003). Published by Lippincott Williams & Wilkins, USA.

Schmidt MA, Yang GZ, Gatehouse PD, Firmin DN. "FID-based lung MRI at 0.5T theoretical considerations and practical implications." *Magn Reson Med* 1998; 39: 666-672. Published by Williams & Wilkins, Baltimore, MD, USA.

Smith F.W., Clinical Application of NMR Tomographic Imaging. Bowman Gray School of Medicine, Winston Salem, North Carolina (1982) pp. 125-132.

Thulborn KR, David D, Adams H, Gindin T, Zhoru J. Quantitative tissue sodium concentration mapping of the growth of focal cerebral tumors with sodium magnetic resonance imaging. *Magn Reson Med* 1999; 41: 351-359.

Waldman, A., et al., " MRI of the brain with ultra-short echo-time pulse sequences" *Neuroradiology.* 2003. [online ], [Retrieved from the Interned Apr. 7, 2004] <URL:http://www.springerlink.com/media/d089tnwvul64k8xvnnr7/Contributions/5/L/G/8/5LG8MX04YGH514 (11pages).

Young, et al., "Magnetic resonance: new approaches to imaging of the musculoskeletal system" Institute of Physics Publishing, Physiological Measurement 24 (2003) R1-R23. [Published online Oct. 13, 2003] Retrieved from the Internet <URL:http://stacks.iop.org/PM/24/R1>.

* cited by examiner

2μs/POINT

4μs/POINT

8μs/POINT

16μs/POINT

 
*FIG. 14A*          *FIG. 14B*

MAGNETIC RESONANCE IMAGING WITH ULTRA SHORT ECHO TIMES

CROSS REFERENCE TO RELATED APPLICATION

This application claims the benefit of priority to International Patent Application No. PCT/US2004/029507, filed September 8, 2004, which further claims the benefit of U.S. Provisional Pat. Application Ser. No. 60/501,451, filed September 8, 2003, entitled MAGNETIC RESONANCE IMAGING WITH ULTRA SHORT ECHO TIMES, entirety of which are incorporated herein by reference as part of the specification of this application.

TECHNICAL FIELD

This application relates to magnetic resonance imaging (MRI) techniques and their applications.

BACKGROUND

A typical MRI technique produces an image of a selected body part of an object under examination by manipulating the magnetic spins of hydrogen atoms or protons in body parts such as fat and water molecules and measuring the signals of the manipulated magnetic spins. The measured responses from the magnetic spins are processed to extract images. A MRI system may be designed to generate different magnetic fields for imaging, including a static magnetic field ($B_0$) along a z-direction to polarize the magnetic spins, gradient fields along mutually orthogonal x, y, or z directions in a xyz coordinate system to spatially select a body part for imaging, and a radiofrequency (RF) magnetic field ($B_1$) to manipulate the spins. MRI techniques may be used to capture the functional changes in body parts or tissues such as the brain perfusion.

In MRI, various characteristic times are generally referred to as $T_1$, $T_2$, $T_2^*$, TR, TI, and TE. $T_1$ designates the spin-lattice relaxation time, $T_2$ designates the spin-spin relaxation time, and $T_2^*$ designates the relaxation time in the transverse plane (with contributions from spin-spin relation, as well as other factors causing de-phasing in the transverse plane). TR designates a repetition time, TI designates an inversion time, and TE designates the echo time.

SUMMARY

This application describes, among others, MRI techniques and systems that use ultra-short echo times, including methods, computer programs, and apparatus as described in the claims.

In general, in one aspect, a method includes sending an excitation RF pulse and a slice selection gradient pulse to selectively excite a target, the slice selection gradient pulse in a first direction. The method further includes subsequently acquiring data from the target to produce a first set of data, reversing the slice selection gradient pulse from the first direction to a second, opposite direction to selectively excite the target, and acquiring data subsequent to the reversed slice selection gradient pulse to produce a second set of data. The excitation RF pulse and the slice selection gradient pulse may be shorter than a short $T_2$ time in the target. The first and second sets of data may be added to construct radial imaging of a corresponding k-space without rephasing of the slice selective excitation RF pulse.

The method may further include quickly reducing the slice selection gradient at an end of the excitation RF The method may further include reducing long $T_2$ components to enhance an image of short $T_2$ components. Acquiring the data may be initiated after the excitation RF pulse and the slice selection gradient are ramped down to zero.

In general, in another aspect, a method may include generating an inversion pulse to substantially invert magnetic moments of a first component of a sample, the first component having a first $T_2$, and wherein the sample further includes a second component having a second $T_2$ less than the first $T_2$. The method may further include, after an inversion time TI, generating an ultra-short TE pulse sequence to selectively excite magnetic moments in a first slice of the sample. The method may further include detecting a generated signal based on the selective excitation of the magnetic moments in the first slice of the sample, and wherein TI is selected to reduce a contribution to the generated signal from magnetic moments of the first component with respect to the second component.

In general, in another aspect, a method of magnetic resonance imaging, may include generating a fat suppression pulse to excite magnetic moments of a fat component of a sample, wherein the sample further includes a first component having a first $T_2$ and a second component having a second T2 less than the first $T_2$. The method may further include generating a 90 degree pulse to rotate magnetic moments of a first component of the sample having a first T2 90 degrees. The method may further include generating a dephasing gradient pulse to de-phase magnetic moments of the first component of the sample. The method may further include generating an ultra-short TE pulse sequence to selectively excite magnetic moments included in the first slice of the sample, and detecting a generated signal based on the selective excitation of the magnetic moments in the first slice of the sample.

In general, in another aspect, an apparatus for magnetic imaging may include a magnet to generate an RF field, the magnet configured to generate an RF field having a magnitude of 30 microTesla or greater. The apparatus may further include a magnet controller in communication with the magnet. The magnet controller configured to cause the magnet to generate an excitation RF pulse and a slice selection gradient pulse, the slice selection gradient pulse in a first direction, the slice selection gradient pulse having a gradient slew rate and a gradient strength; and subsequently reverse the slice selection gradient pulse from the first direction to a second, opposite direction.

In general, in another aspect, one or more computer programs may be include instructions that, when executed by one or more machines, results in the operations described above.

The details of one or more implementations are set forth in the accompanying drawings and the description below. Other features and advantages will be apparent from the description and drawings, and from the claims.

DESCRIPTION OF DRAWINGS

FIGS. 14A to 14D show images of a fracture of the tibial plateau three days after injury.

Like reference symbols in the various drawings indicate like elements.

DETAILED DESCRIPTION

Various conventional MRI systems and techniques may be inadequate to image certain components with short $T_2$ times. Imaging short $T_2$ components of tissues and other samples is desirable in various clinical diagnostic applications. The ability to image both shorter and longer $T_2$ components may be beneficial as well.

Systems and techniques described herein may provide for performing magnetic resonance of samples having components with short $T_2$'s. For example, exemplary MRI techniques for performing clinical ultra-short TE (UTE) pulse sequences in imaging tissues or tissue components with short $T_2$'s are described. In some implementations, target tissues may be divided into tissues with a majority of short $T_2$ relaxation components and tissues with a minority of short $T_2$'s. Systems and techniques provided herein may be used to increase contrast between short $T_2$ and long $T_2$ tissue components.

Figure 1A:
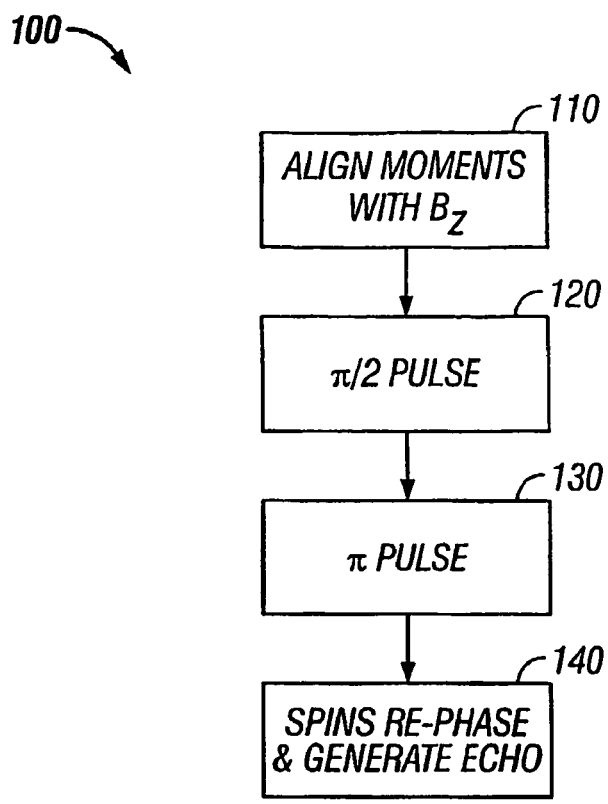
FIG. 1A illustrates a spin-echo process.
Figure 1B:
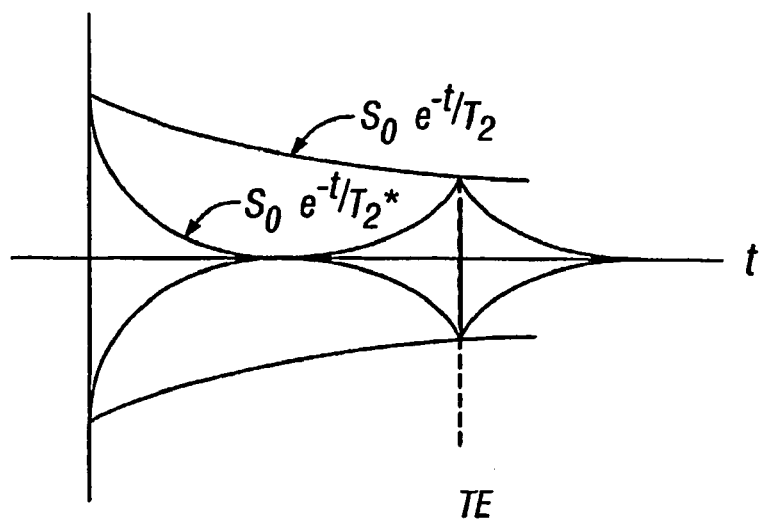
FIG. 1B shows a signal that may be generated by a system as a result of the spin-echo process of FIG. 1A.

For traditional, relatively long $T_2$ imaging, spin-echo techniques may be used. FIG. 1A shows an example of a spin-echo process 100 that may be used to determine $T_2$ of samples with relatively long $T_2$'s. At 110, the z-components of the magnetic moments of the sample nuclei are generally aligned with an external longitudinal (z-direction) magnetic field, $B_0$. At 120, a $\pi/2$ pulse is applied. That is, an RF pulse is applied for a time sufficient to rotate the magnetization of the spins into the transverse plane. Once rotated, the spins begin to de-phase. At 130, a $\pi$ pulse is applied. After the $\pi$ pulse, the spins begin to re-phase. At 140, the spins return to the initial phase state, and a measurement of the magnetization shows a peak. The peak occurs at a time referred to as the echo time, TE. FIG. 1B shows a signal that may be measured using a spin-echo technique. Both $T_2^*$ and $T_2$ may be determined using the envelopes of the detected signals. Note that many types and variations of pulse sequences may be used for MRI imaging.

Figure 1C:
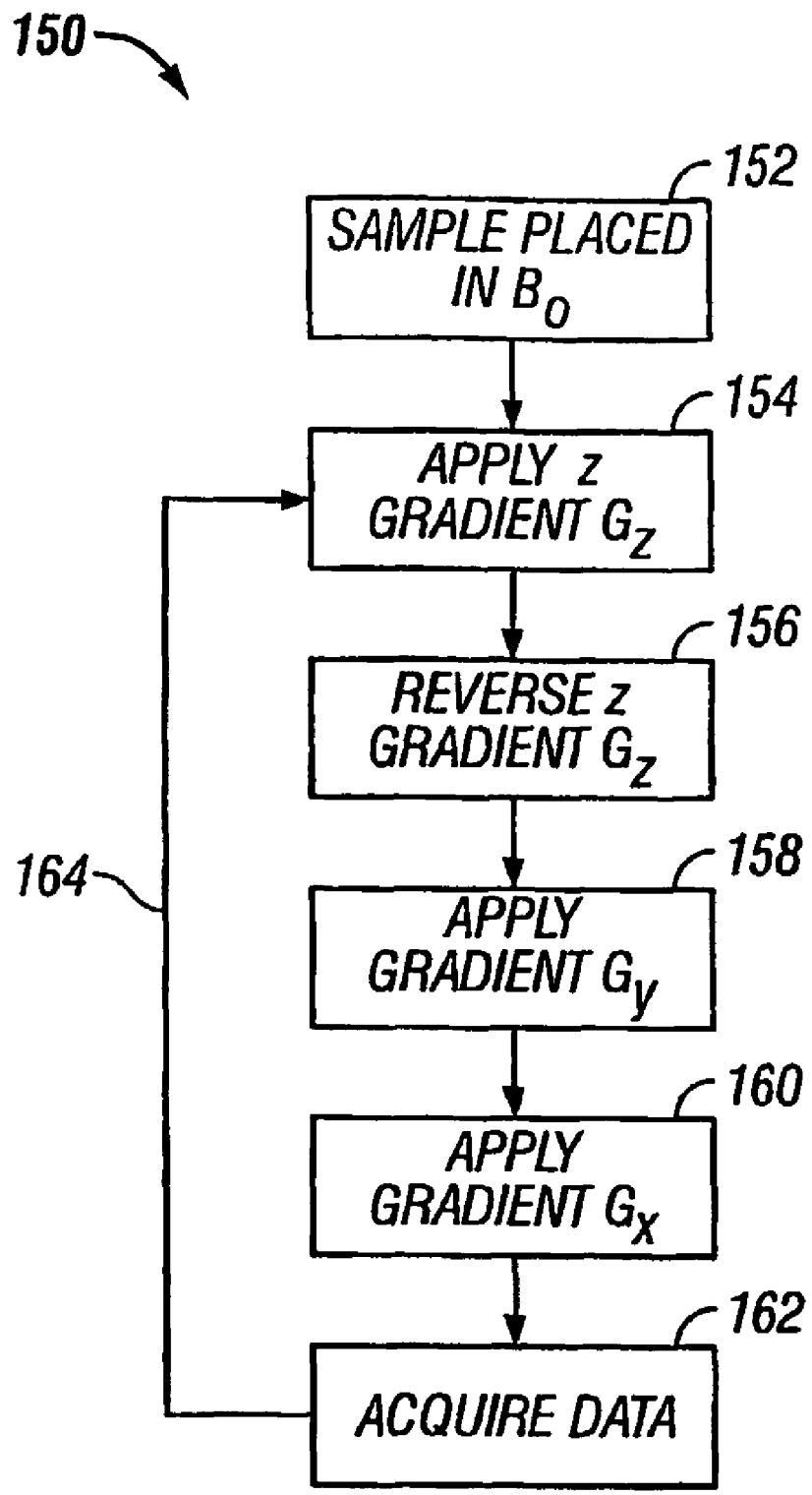
FIG. 1C illustrates a gradient echo process.

For some types of MRI studies, such as medical imaging, slice selective MRI may be used to selectively image slices of the tissue. One example of slice selective MRI is a gradient echo imaging method. FIG. 1C shows an example of a process 150 that may be used to image slices using gradient echo imaging. At 152, the sample to be imaged is placed in a magnetic field $B_0$. At 154, a constant z-gradient is applied during the RF pulse for a total time $\tau_{rf}$. At 156, the Z-gradient is reversed immediately following the pulse. At the end of the re-phase lobe of the slice select gradient, the transverse magnetization components in the slice are in phase. At 158, after the slice select gradient is turned off, it is followed by a phase encoding gradient $G_y$. At 160, a gradient $G_x$, is applied, with a negative dephasing lobe followed by a read (or re-phasing) lobe. At 162, the signal is detected to determine properties of the particular selected slice. At 164, the process is repeated, with the phase encoding gradient $G_y$ stepped through different values.

Figure 2A:
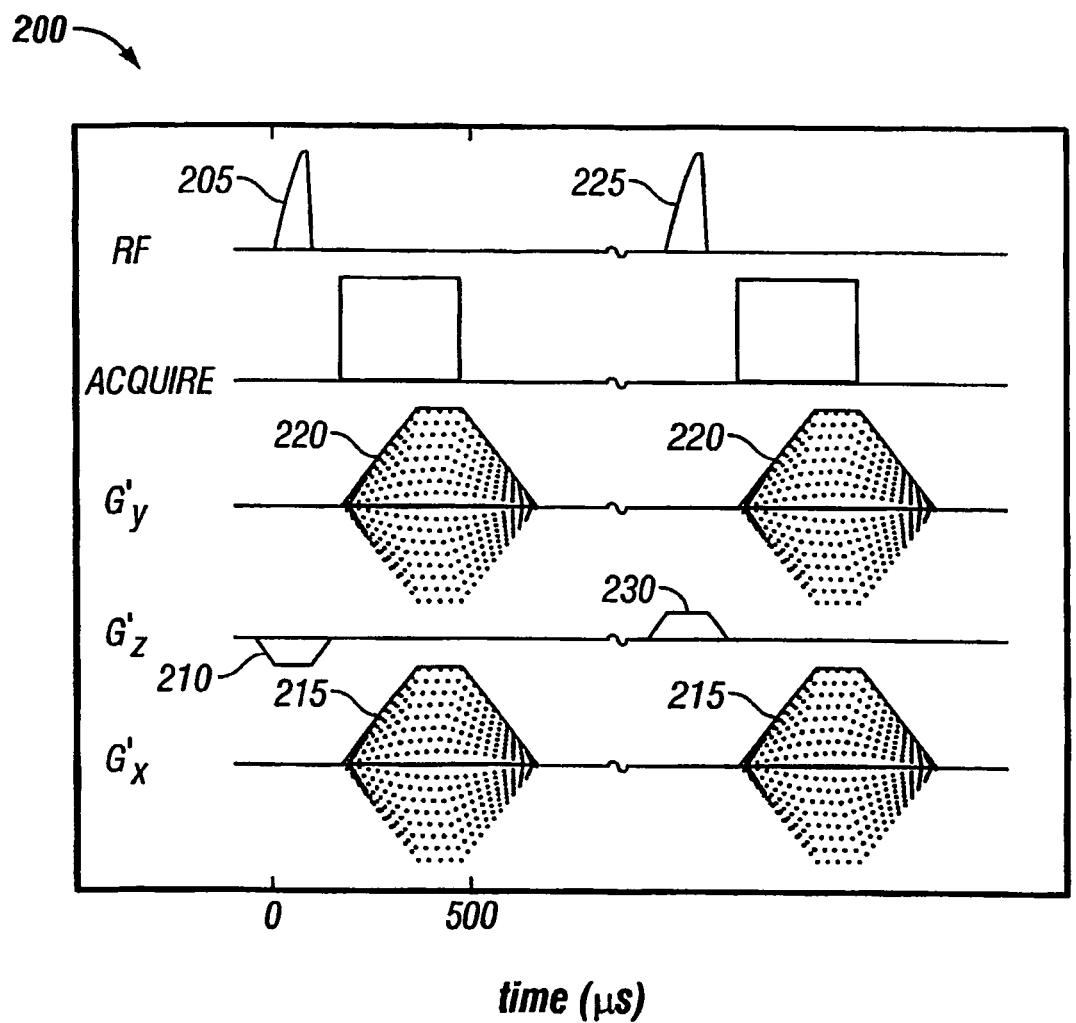
FIG. 2A illustrates an ultra-short TE (UTE) pulse sequence.

In order to image samples that include components with short $T_2$'s, techniques referred to as ultra-short TE techniques (UTE) may be used. FIG. 2A shows an example of a pulse sequence 200 for UTE imaging.

A first, half RF pulse 205 is applied, followed by radial imaging of k-space from the center out. For the first acquisition, the z gradient $G'_z$ 210 is negative. The RF pulse is truncated and followed rapidly by the acquisition, during which $G'_x$ 215 and $G'_y$ 220 are applied to provide the radial gradient. A second, half RF pulse 225 is applied, with the z gradient $G'_z$ 230 positive. The RF pulse is again truncated, and the second acquisition is performed. During the second acquisition, $G'_x$ 215 and $G'_y$ 220 are again applied to provide the radial gradient. The two sets of data are added to give a single line of k-space, and the process repeated to acquire an image of the desired resolution.

Figure 2B:
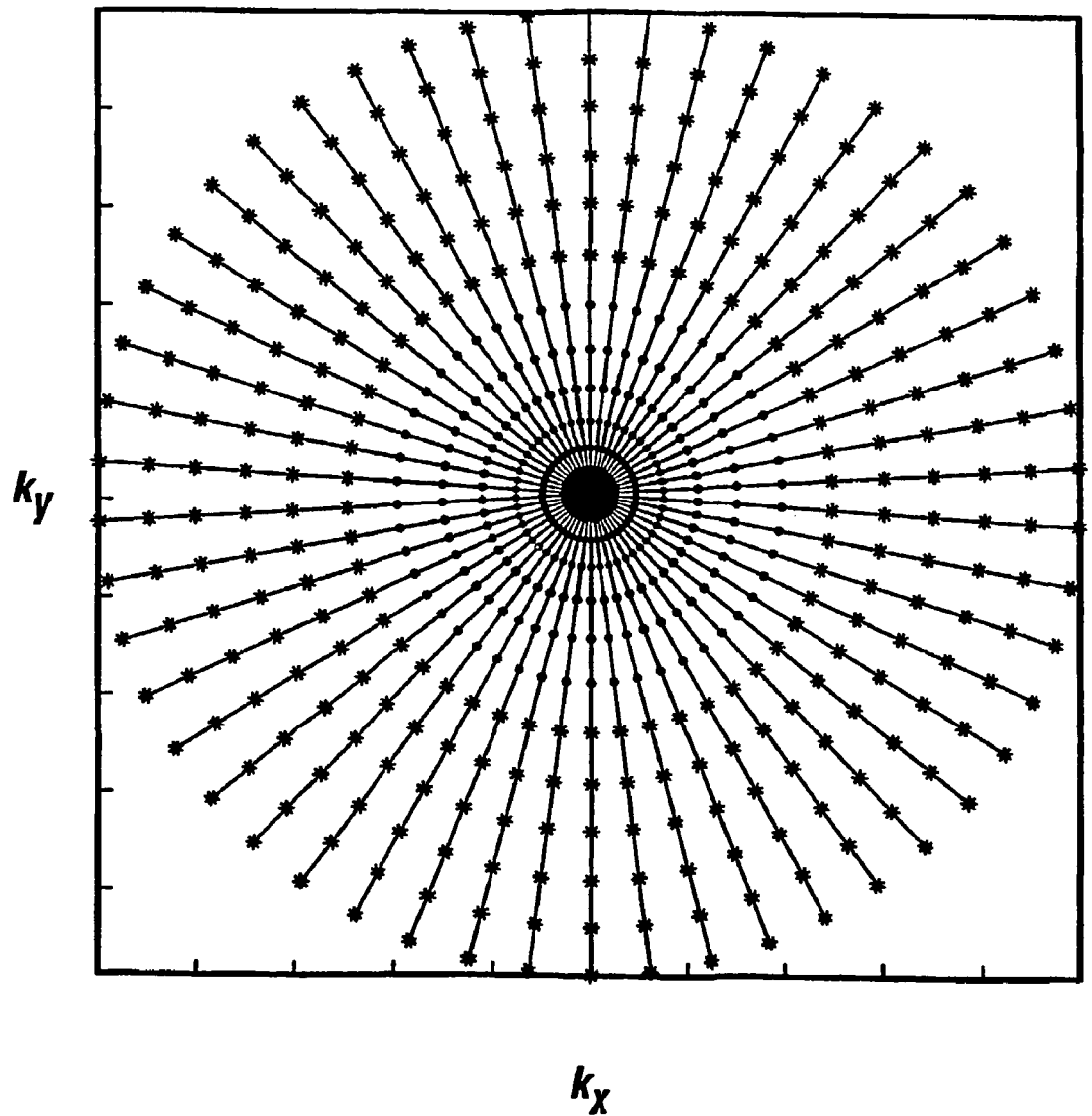
FIG. 2B illustrates exemplary k-space trajectories that may be obtained using a UTE pulse sequence such as that of FIG. 2A.

FIG. 2B shows exemplary k-space trajectories that may be obtained using pulse sequence 200 of FIG. 2A. Each spoke represents the k-space trajectory due to the readout gradients. The dots represent the central points which are sampled on the gradient ramps, and the stars the peripheral points which are sampled on the gradient plateau. In some implementations, data acquisition includes 128-512 spokes and 256-512 points per spoke. The data points are generally re-gridded onto a Cartesian grid prior to 2D Fourier transformation.

Figure 2C:
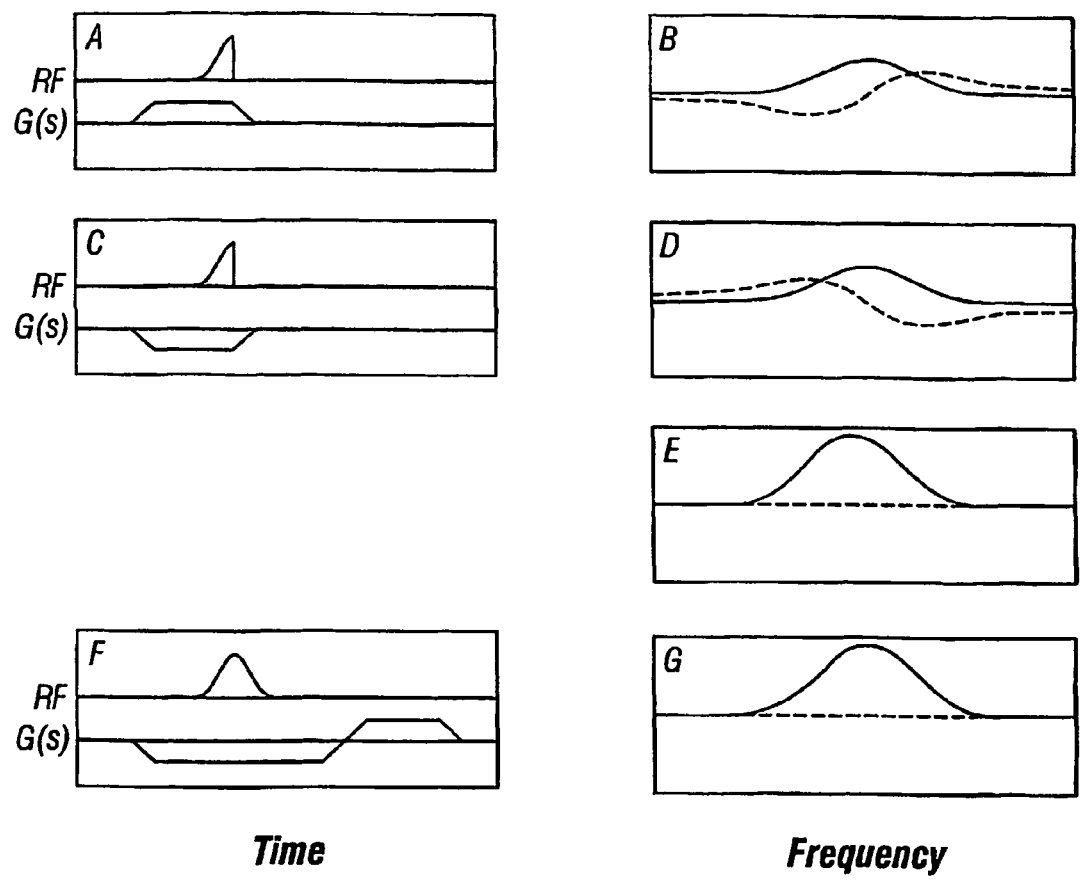
FIG. 2C shows a UTE slice profile.

FIG. 2C shows slice profiles obtained using a pulse sequence such as that shown in FIG. 2A. The two half pulse excitations are denoted by (A) and (C). The slice profiles from these acquisitions are shown in (B) and (D), respectively, where the continuous line is the real component and the dashed line is the imaginary component. If the data in (B) and (D) are added in the complex domain, a narrow profile is obtained, as shown in (E). Conventional sequence slice selection (F) produces the profile shown in (G), which is the same as the profile shown in (E). The need for short RF pulses predicates against a sharp edged slice profile.

A number of additional techniques may be used with an ultra-short TE pulse sequence such as sequence 200 of FIG. 2A. For example, techniques for suppressing unwanted signals (such as signals from longer $T_2$ components and signals from fat) may be used. To suppress longer T2 components and increase signal to noise ratio, inversion pulse techniques may be used. In an example, a pulse configured to invert longer $T_2$ components may be generated. After an inversion time TI, the ultra-short TE pulse sequence may be generated. The inversion time TI is selected to reduce a contribution to the signal from the longer $T_2$ components.

In another technique, fat suppression may be combined with long $T_2$ suppression. A fat suppression pulse may be generated. In order to suppress signal from longer $T_2$ components, a 90 degree pulse may be generated to rotate the spins into the transverse plane. A gradient pulse may then be generated to de-phase the spins of the longer $T_2$ components, thus reducing their signal contribution.

In another technique, additional pulse sequences may be used in addition to one or more ultra-short TE pulse sequences. For example, an echo sequence such as a spin echo sequence or a gradient echo sequence may be generated. Data generated as a result of the echo sequence may be used to create a difference image by subtracting it from associated data of an ultra-short TE pulse sequence. In some implementations, multiple echo sequences may be implemented.

Artifacts may also be reduced. For example, anti-aliasing techniques and/or random sampling may be used to reduce image artifacts. Contributions due to motion may be reduced using gating techniques. For example, pulse sequences may be generated based on a gate signal related to a cardiac signal and/or a breath hold signal. Contrast agents may be used to increase contrast.

The UTE pulse sequences may be used to image thin slices. For example, slices as thin as about 2 mm or less may be imaged. In some implementations, other slice thicknesses may be imaged. For example, slices between about 2 mm and about 4 mm, or slices between about 4 mm and about 8 mm. The UTE pulse sequences described herein may be characterized by an echo time TE of about 80 microseconds or less.

A number of exemplary systems and techniques for performing UTE imagining are discussed herein. Table 1 below outlines some acronyms and abbreviations used to discuss these systems and techniques, as well acronyms for other MRI-related terms.

TABLE 1

| Acronym/abbreviation | Refers to |
| --- | --- |
| UTE | Ultrashort TE |
| CUTE | Conventional ultrashort TE |
| FUTE | Fat suppressed ultrashort TE |
| LUTE | Long $T_2$ suppressed ultrashort TE |
| FLUTE | Fat and long $T_2$ suppressed ultrashort TE |
| STUTE | Short TI inversion time ultrashort TE |
| MUTE | Medium TI inversion time ultrashort TE |

TABLE 1-continued

| Acronym/abbreviation | Refers to |
| --- | --- |
| d | difference image produced by subtraction of a subsequent image from the first |
| l | Long inversion pulse (used with STUTE and MUTE sequences) |
| s | Short inversion pulse (used with STUTE and MUTE sequences) |
| FT | Fourier Transform |
| TR | Repetition time |
| FLAIR | Fluid attenuated inversion recovery |
| 2DFT | Two dimensional Fourier Transform |

Features of the basic physics relevant to UTE imaging are described herein, including the fact when the RF pulse duration is of the order of $T_2$, rotation of tissue magnetization into the transverse plane is incomplete. Consequences of the broad linewidth of short $T_2$ components are also discussed, including their partial saturation by off-resonance fat suppression pulses as well as multi-slice and multi-echo imaging. The benefits of rapid data acquisition-for example, on the order of $T_2$-are also detailed.

In some implementations, a basic UTE pulse sequence including a half excitation pulse and radial imaging from the center of k-space may be used. In some implementations, other techniques may be used as well; for example, techniques for suppressing signals due to fat and/or signals due to relatively long $T_2$ components.

Image interpretation is discussed. Clinical features of the imaging of cortical bone, tendons, ligaments, menisci and periosteum as well as brain, liver and spine are illustrated. Short $T_2$ components in all of these tissues may show high signals.

An effective strategy for diagnosis of parenchymal disease with magnetic resonance (MR) imaging is the use of heavily $T_2$ weighted pulse sequences to detect an increase or decrease in signal from abnormal tissue. Even with newer pulse sequences such as fast spin echo, echo planar imaging, fluid attenuated inversion recovery (FLAIR) and diffusion weighted imaging, the main diagnostic emphasis remains on detecting signal from tissues with long $T_2$'s.

From the earliest days of clinical MR it was recognized that there were also tissues such as cortical bone which had short $T_2$'s. The MR signal from these tissues characteristically decays very rapidly, so that with the echo times (TE's) used in conventional clinical imaging they produce little or no signal, and so appear generally dark.

The low signal from cortical bone and other tissues with a short $T_2$ provides a useful background against which to recognize abnormalities which produce an increase in signal. A disadvantage of this approach is that the absence of signal in the normal tissue means that there is little opportunity to manipulate conspicuity by using different pulse sequences or contrast agents. Clinically it has been difficult, and in certain cases not been possible, to characterize these tissues in MR terms, for example, by measuring their $T_1$'s and $T_2$'s.

While tissues such as cortical bone, tendons, ligaments and menisci contain a majority of short $T_2$ components, other tissues also contain short $T_2$ components, but as a minority species. Signal from the short $T_2$ components in these tissues may be difficult to detect. For example, with some conventional clinical pulse sequences, the MR signal comes from the majority of long $T_2$ components.

In quantitative terms, using conventional 2D Fourier transform (2DFT) imaging with basic spin echo imaging sequences (with TE's down to about 8-10 ms), tissues with $T_2$'s shorter than about 10 ms have not generally been detectable. Shorter TE's (for example, in the range of about 1-2 ms) may now be achieved using fast 2DFT gradient echo pulse sequences, which may lower the limit of detectable $T_2$'s to a range of about 1-2 ms.

Pulse sequences with even shorter TE's (for example, in the range of approximately 0.05-0.20 ms) can be produced by use of half radiofrequency (RF) excitations with radial mapping from the center of k-space. These ultrashort TE (UTE) pulse sequences, have TE's about 10 to 20 times shorter than the shortest generally available on modern clinical systems. With these sequences, short $T_2$ components found in cortical bone may be the largest contributors to the MR signal, despite their short $T_2$ (about 0.42-0.50 ms).

Figure 3:
FIG. 3 shows a transverse image of a normal tibia.

FIG. 3 shows a transverse image of a normal tibia. The image was obtained using ds STUTE techniques with magnitude reconstruction. TR/TE/TI were 650/0.08 minus 5.95/80 ms. Cortical bone is highlighted. It is surrounded by a dark cancellation line and low signal from adjacent muscle and fat. The $T_1$ of cortical bone (130 ms) is shorter than other tissue in the image.

What applies to cortical bone also applies to other tissues with a majority of short $T_2$ components. In addition, using UTE pulse sequences, signal can be specifically detected from the short $T_2$ components in tissues in which they are in a minority. For reference, ranges of TE's with different pulse sequences are listed in Table 2.

TABLE 2

| TE Description | TE Values | Examples |
|---|---|---|
| Very long | 200 ms and longer | 2DFT, HASTE, fast spin echo and EPI; very heavily long $T_2$ weighted |
| Long | 20-40 to 200 ms | 2DFT, HASTE, FLAIR, fast spin echo, EPI; heavily long $T_2$ weighted |
| Intermediate | 5-10 to 20-40 ms | 2DFT; $T_1$ weighted or proton density weighted |
| Short | 0.5 to 5-10 ms | 2DFT; $T_1$ weighted |
| Ultrashort | 0.05 to 0.50 ms | Half RF pulse with radial center out sampling; short $T_2$ weighted |

Note that the weighting depends on the $T_1$ and $T_2$ of the tissue or fluid of interest. In this paper the term ultrashort has been used specifically to describe radial methods of data acquisition with TE's less than about 0.50 ms, although in the literature the terms ultrashort and short are not uniformly defined.

In the course of developing the techniques described here, studies of 120 patients were conducted to test their clinical use in proton imaging. Results of these studies are described in this application There has been a large volume of work published on the MR properties of tissue. Some tissue properties are important for imaging of short $T_2$ components.

For the examples described here, we have used the term "short $T_2$" to refer to $T_2$ values of less than 10 ms. This, however, is intended as an example to illustrate the techniques of this application. Prior to the techniques outlined in this application, $T_2$ values of less than 10 ms would have corresponded to the limit of clinical detectability with basic spin echo sequences. However, using UTE sequences, most tissues with short $T_2$'s are detectable. The lower limit of useful detectability with UTE sequences may be between 0.1 and 0.01 ms or lower, which is two orders of magnitude shorter than the earlier limit of about 10 ms, and an order of magnitude shorter than that with 2DFT gradient echo images. The limit closely parallels TE. Much of the discussion which follows relates to short $T_2$'s in the lower short $T_2$ range down to the limit of detectability with UTE sequences. The term extremely short can be applied to tissues which have $T_2$'s shorter than this limit such as those in solids, proteins and other macromolecules. Estimated mean $T_2$'s of some adult tissues and tissue components with short $T_2$'s are listed in Table 3.

TABLE 3

| Tissue or Tissue Component | Mean $T_2$ |
|---|---|
| Ligaments | 4-10 ms |
| Achilles tendon | 0.25 and 0.7 ms, 1.2 ± 0.2 ms, 0.53 ms (88%) and 4.8 ms (12%), 7 ms |
| Knee menisci | 5-8 ms |
| Periosteum | 5-11 ms |
| Cortical bone | 0.4-0.5 ms |
| Dentine | 0.15 ms |
| Dental enamel | 70 μs |
| Protons in water tightly bound to proteins | 10 μs |
| Protons in proteins | 10 μs |
| Protons in solids e.g. calcium hydroxy appatite | 1 μs or less |

The sources for the data of Table 3 were adult clinical results, as well as tissue sample results estimated for 1.5 T. Tissues with long $T_2$'s which undergo significant dephasing (such as nasal sinus mucosa) may have short $T_2^*$'s (<10 ms) and thus appears similar to tissues with short $T_2$'s.

It may be assumed that all tissues are heterogeneous and have components with different values of $T_2$. For protons this follows from the fact that tissues contain protons in proteins (with very short $T_2$'s of about 10 μs, or 0.01 ms) as well as protons in water with much longer $T_2$'s. As a first approximation it is then possible to describe tissues as having both short and long $T_2$ components, although most if not all tissues have more than two components (and thus more than two different $T_2$ values). Although two component samples are discussed herein, the principles may be extended to embrace samples with three or more components (and thus, three or more applicable $T_2$ values). As noted above, for the purposes of discussion, samples may be divided into those having a majority of short $T_2$ components and those having a minority of short $T_2$ components. Table 4 lists tissue types having a majority of short $T_2$ components. Most other tissue types have a minority of short $T_2$ components.

TABLE 4

| Meninges (dura) | Falx | Tentorium |
|---|---|---|
| Membranes | Capsules | Bands |
| Retinaculi | Septae | Fascae |
| Sheaths | Nails | Hair |
| Aponeuroses | Tendons | Ligaments |
| Menisci | Labrii | Periosteum |
| Bone | Dentine | Enamel |

As shown in Table 4, the tissues with a majority of short $T_2$ components include cortical bone, dentine and enamel (very short $T_2$'s and always zero signal with conventional sequences) as well as other tissues where signal is low with conventional sequences but not always zero. The many tissues with a minority of short $T_2$ components such as skeletal muscle, white matter and gray matter of the brain have these components present in low concentrations, typically of about 1-20%. Magnetization decay curves for these two groups of tissues are shown using conventional TE and UTE sequences in FIGS. 4A, 4B, 5A, and 5B.

Figure 4A:
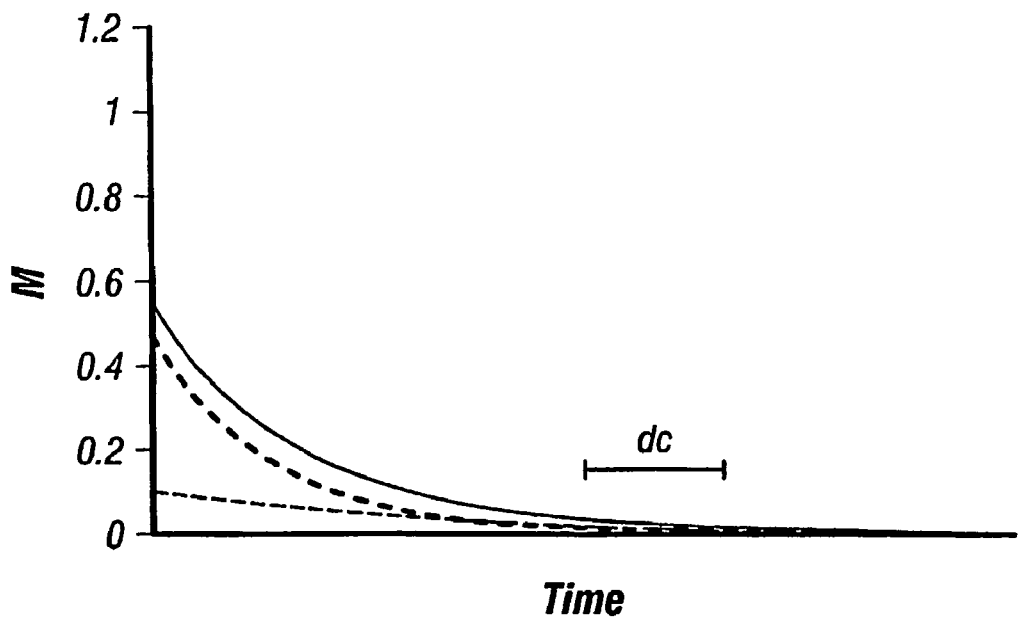
FIG. 4A shows transverse magnetization decay for a tissue with a majority of short $T_2$ components imaged with a conventional pulse sequence.
Figure 4B:
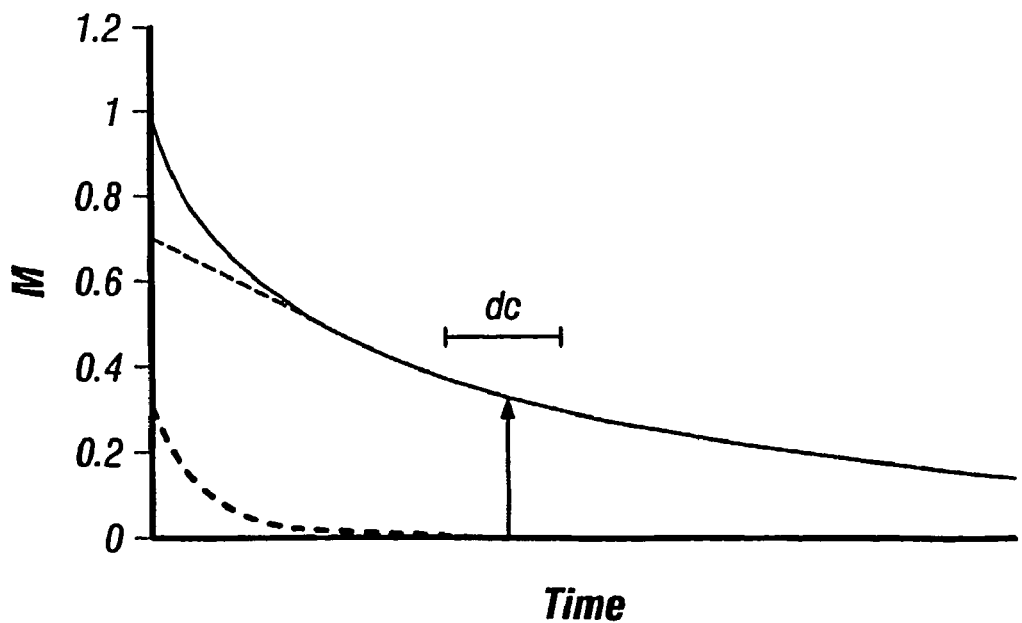
FIG. 4B shows transverse magnetization decay for a tissue with a minority of short $T_2$ components imaged with a conventional pulse sequence.

FIGS. 4A and 4B show transverse magnetization decay for a tissue with a majority of short $T_2$ components (FIG. 4A) and a minority of short $T_2$ components (FIG. 4B) imaged with a conventional pulse sequence TE. The continuous line represents the total magnetization, the circles that of the short $T_2$ components, and the dashes that of the long $T_2$ components. In FIG. 4A, the signal has largely decayed to zero by the time of the data collection (dc) at TE and little or no signal is detected. In FIG. 4B the magnetization of the short $T_2$ components has decayed to zero by the time of data collection at TE, but that of the long $T_2$ components persists, and provides the detectable signal represented by the vertical arrow.

Figure 5A:
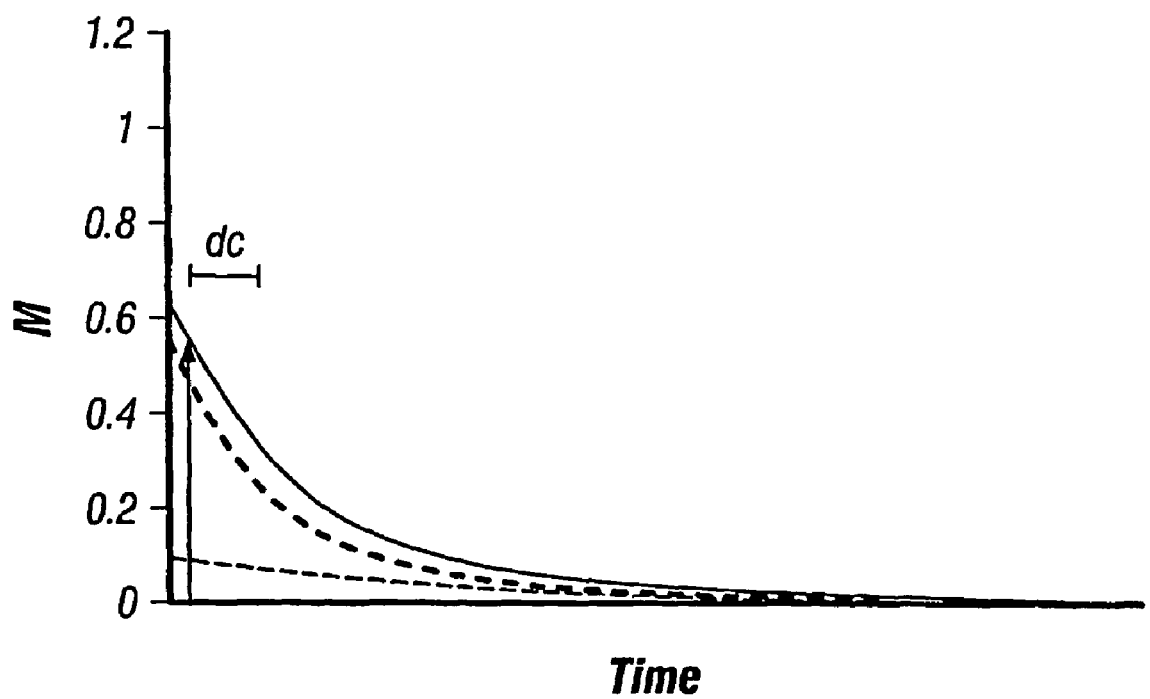
FIG. 5A shows transverse magnetization decay for a tissue with a majority of short $T_2$ components imaged with a UTE sequence.
Figure 5B:
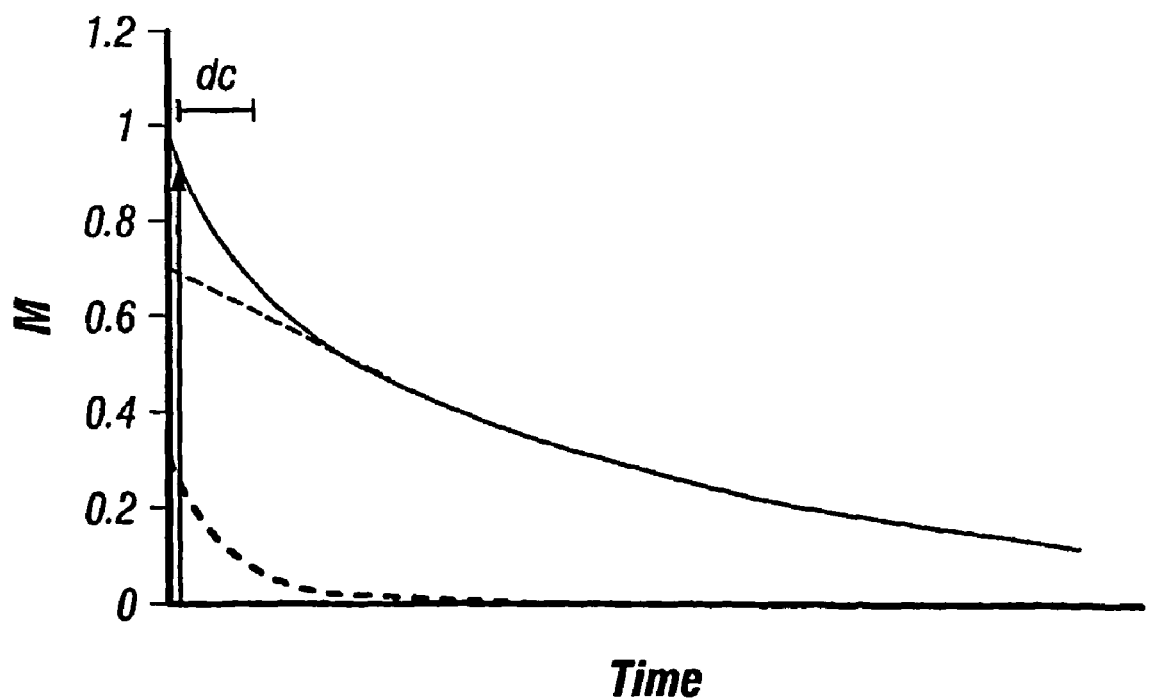
FIG. 5B shows transverse magnetization decay for a tissue with a minority of short $T_2$ components imaged with a ultra-short TE pulse sequence.

FIGS. 5A and 5B show transverse magnetization decay for a tissue with a majority of short $T_2$ components (FIG. 5A) and a tissue with a minority of short $T_2$ components (FIG. 5B) imaged with a UTE pulse sequence with the data collection at a shorter TE and much earlier than in FIGS. 4A and 4B. In comparison to FIGS. 4A and 4B, the magnetization of the short $T_2$ components is now detectable in FIG. 5A, and magnetization of both the short and long $T_2$ components is detectable in FIG. 5B.

There can be a number of causes for short $T_2$'s in tissues. In general, solids have very short $T_2$'s as a result of the strong dipolar interactions between substantially immobile nuclei. Protons in the crystalline component of bone have extremely short $T_2$'s (less than 1 µs). Protons in macromolecules within membranes or in water closely bound to them are also relatively immobile and have short $T_2$'s. Protons in water which is less tightly bound to large molecules have longer $T_2$'s, eventually extending up to that of free water which has a $T_2$ of about four seconds.

Another cause of short $T_2$'s is susceptibility effects in tissues which are diamagnetic or paramagnetic to different degrees so that their nuclei experience slightly different magnetic fields. This results in a net dephasing, with an attendant loss of signal. These magnetic interactions may be the dominant mechanism for producing short $T_2$'s in a number of situations, particularly those involving paramagnetic species. Diffusion of water molecules in magnetically inhomogeneous tissue is another potential cause of short $T_2$'s.

Tissues such as tendons and ligaments which contain a high proportion of linearly ordered collagen are of particular interest. Protons in water bound to collagen in these tissues typically manifest strong dipolar interactions which, unlike those in water bound to proteins in general, are dependent on the macroscopic orientation of the collagen fibres to the static magnetic field, $B_0$. Their dipolar interactions are modulated by the term $(3 \cos^2 \theta - 1)$ where θ is the angle the collagen fibres make to $B_0$. Where $\theta=55°$, 125° etc. (the magic angle), $3 \cos^2 \theta - 1 = 0$, dipolar interactions are minimized and so $T_2$ is increased. This effect has been recognized as a source of artifact in musculoskeletal imaging where tendons and ligaments may show a high signal when all or part of them happens to be orientated at 55° to $B_0$. It can also be used as a technique for increasing the $T_2$ of tendons (e.g. from about 7 to about 23 ms) to bring their signal into the detectable range when imaging with conventional spin echo pulse sequence TE's.

Although lung was the first tissue imaged with UTE pulse sequences it is a rather special case. It has a low proton density, is particularly prone to susceptibility effects at lung-air interfaces, a large proportion of the signal comes from flowing blood and it is subject to respiratory motion. These make imaging of its short $T_2$ components a considerable technical challenge.

In disease a variety of processes may increase the signal from short $T_2$ components e.g. chronic fibrosis, calcification, components of hemorrhage at various stages, cellular infiltration, deposition of short $T_2$ tissues (e.g. amyloid), iron deposition, deposition of other paramagnetics, malignant melanoma, thrombosis clots and emboli, cryoablation and administration of magnetic iron oxide particles (MIOP's). These processes may increase the concentration of the short $T_2$ components by the addition of new tissue with a short $T_2$ as well as by shortening the $T_2$'s of the long $T_2$ components in tissue. The signal from short $T_2$ components may also be increased by shortening their $T_1$.

There are also many processes which may decrease the signal from short $T_2$ components. These include many of the diseases which typically increase tissue $T_1$'s and $T_2$'s such as edema, acute inflammation, infection, infarction and many tumors. Loss of order in a highly structured tissue such as collagen may also lead to a decrease in signal from its short $T_2$ components. Reduction in signal from $T_2$ components may also result from a decrease in their concentration, a decrease in their $T_2$ into the extremely short $T_2$ range and an increase in their $T_1$.

This section outlines features of the MR physics which particularly apply to UTE imaging. During any radiofrequency (RF) pulse there is competition between the pulse tending to rotate the magnetization into the transverse plane and relaxation processes tending to decrease magnetization in the transverse plane. With long $T_2$ species such as free water, relaxation during the RF pulse is minimal, and the magnetization of the protons is fully rotated through the specified flip angle (e.g. 90°) into the transverse plane.

However with short $T_2$ species, where $T_2$ is of the same magnitude as the duration of the RF pulse or shorter, relaxation processes dominate and the magnetization actually rotated into the transverse plane may be very much less than that expected from the nominal pulse flip angle. At the same time the longitudinal magnetization is partly saturated so that overall there is a reduction of magnetization in the transverse plane with a decrease in the longitudinal direction.

Figure 6:
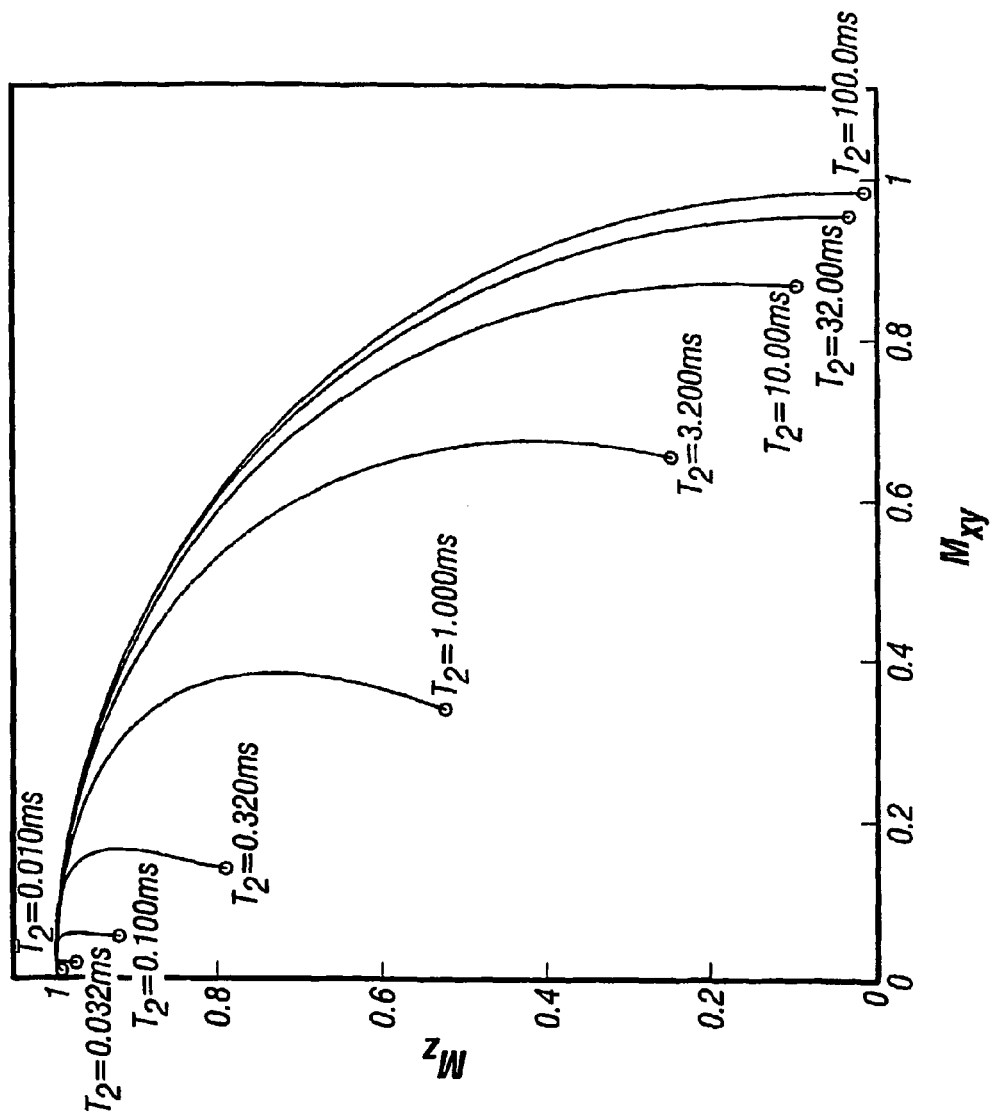
FIG. 6 shows a simulation of a magnetization trajectory.

FIG. 6 shows a simulation of the magnetization trajectory during a 3 ms, 90 degree rectangular pulse, showing rotation of longitudinal magnetization ($M_z$) into the transverse plane to become $M_{xy}$ for tissues with $T_2$'s between 0.01 and 100 ms. For a tissue with a $T_2$ of 100 ms, rotation is almost complete, but as $T_2$ is decreased, less magnetization is rotated. For $T_2=0.01$ ms, there is essentially no magnetization rotated into the transverse plane. $M_z$ is also reduced.

Therefore, in sequences designed for imaging of short $T_2$ species, short RF excitation pulses are used. It also means that the effective duration of an RF pulse is loaded towards its later stages for short $T_2$ species, since these may relax significantly during the earlier stages of the pulse.

In some implementations, this situation may be exploited by purposely using pulses of long duration to selectively rotate long $T_2$ components into the transverse plane but leave short $T_2$ components largely unaffected. For example to reduce the signal from long $T_2$ components, a long duration (e.g. about 10 ms) rectangular 90° pulse may be used to rotate the long $T_2$ components into the transverse plane and then de-phase them with crusher gradients while leaving the short $T_2$ components largely unaffected.

Figure 7:
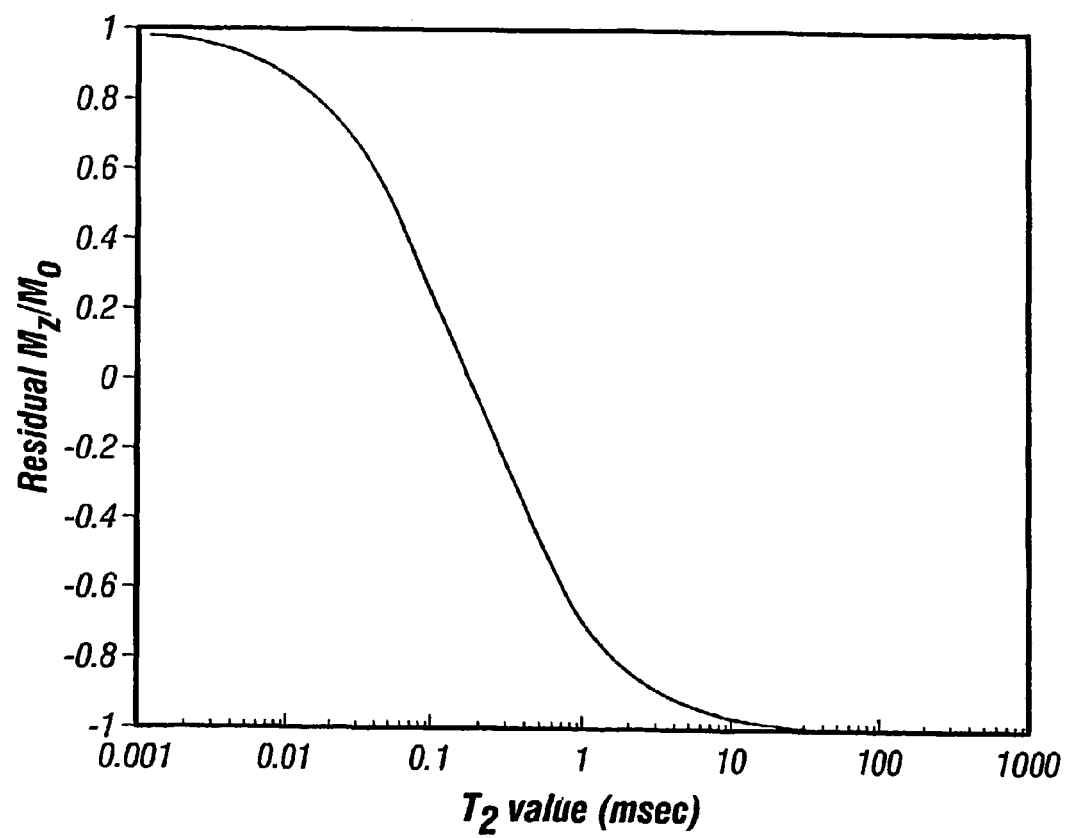
FIG. 7 shows the effect of a short inversion pulse on magnetization.

These considerations not only apply to 90° and lower flip angle pulses, but also to inversion pulses. These are of necessity longer than 90° pulses, and longer again if they are slice selected. Depending on the duration of the pulse, a short $T_2$ tissue may be unaffected, saturated or rotated to various angles less than 180° by such a pulse. FIG. 7 shows the effect of a short inversion pulse (0.50 ms) on magnetization $M_z$, for tissues with different values of $T_2$. The residual magnetization, $M_z/M_0$, present after application of the pulse is plotted against $T_2$. With $T_2$'s of 100 ms or more, the magnetization is almost fully inverted (i.e. $M_z/M_0$ is about equal to negative one). However, for shorter $T_2$'s (e.g., 0.01 ms), very little magnetization is inverted.

While it can be very difficult to invert short $T_2$ components, it is much easier to saturate them. To do this they need to be excited but the dephasing process is then very effective and very short $T_2$ components may not even need a subsequent dephasing gradient pulse. As a result, methods of measuring $T_1$'s of short $T_2$ components which include inversion pulses are difficult, while those utilizing saturation pulses are relatively straightforward.

Figure 8A:
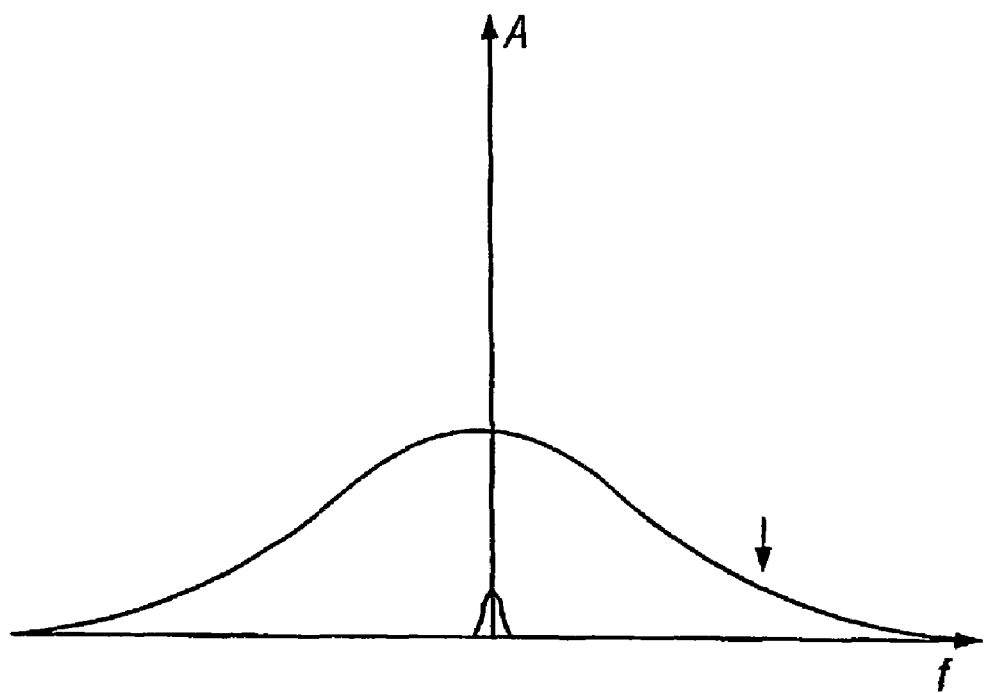
FIG. 8A shows a stylized spectrum of a tissue with a majority of short $T_2$ components.
Figure 8B:
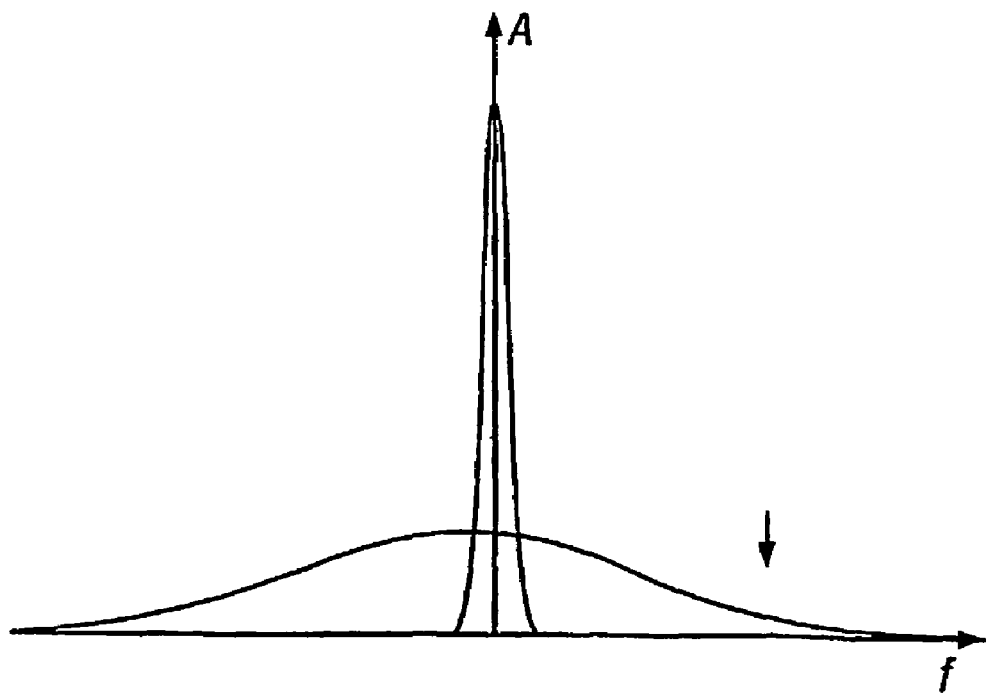
FIG. 8B shows a stylized spectrum of a tissue with a minority of short $T_2$ components.

Another basic difference from conventional MR is the fact that short $T_2$ components have broad linewidths and therefore may be saturated by off-resonance RF pulses. FIGS. 8A and 8B illustrate this principle. FIG. 8A shows a stylized spectrum of a tissue with a majority of short $T_2$ components, while FIG. 8B shows one with a minority of short $T_2$ components. For each, amplitude (A) is plotted versus frequency (f).

The short $T_2$ components have a broad line, while the long $T_2$ components have a narrow line. The off-resonance pulse in (a) (arrow) saturates the broad line and reduces the signal which can be detected from these components with a UTE sequence. The off-resonance pulse in (b) (arrow) saturates the broad line which then exchanges with the larger narrow line (long $T_2$) pool and produces a reduction in the magnetization detected from it with conventional TE sequences. With UTE sequences both the direct saturation of the short $T_2$ components and the indirect effect on the long $T_2$ components via magnetization transfer are detectable.

Saturation of short $T_2$ components may occur in a number of ways. Fat suppression techniques with pulses 220-230 Hz off-resonance (at about 1.5T) are relatively close to the resonant frequency. They may thus partially saturate the broad lines of short $T_2$ components, thereby reducing the signal available from them. For example, the signal may easily be decreased by 10-20% because of this effect.

The use of multislice and multiecho imaging, where slices are selected in different locations by use of different resonance frequency offsets, is another situation where reduction in signal from partial saturation of broad line components may occur. These effects may occur in addition to at least some saturation and signal reduction from short $T_2$ components due to the deliberate application of off-resonance pulses with magnetization transfer (e.g. 1500 Hz off resonance at 1.5T).

There are other differences from conventional imaging. The relatively rapid decay of the signal from short $T_2$ components means that the time available for useful sampling of them is much less than that for long $T_2$ components (which do not decay significantly during a typical data acquisition times, which range from about 10-20 ms). In contrast, the decay of signal attributable to short $T_2$ components during the time during which data is being acquired can result in the loss of high resolution detail. For example, the amplitude of the signal may be sufficient when regions of k-space near the center are being mapped, the amplitude may be significantly lower (or even undetectable) when the outer regions of k-space are mapped.

Figure 9:
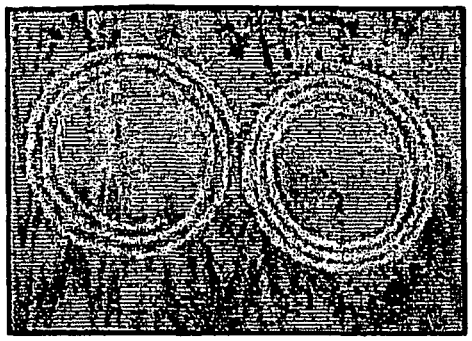
FIG. 9 shows an image of rubber straps and cardboard spacers.
Figure 9:
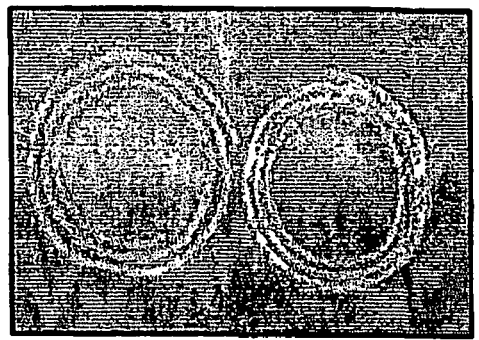
Figure 9:
Figure 9:

FIG. 9 illustrates this effect. FIG. 9 shows CUTE images of two 2 mm thick rubber straps ($T_2$=0.8 ms) wrapped concentrically around 0.5 mm (right) and 1 mm (left) cardboard spacers. The straps gives a detectable signal, while the spacers do not. Images were acquired with 210 mm field of view (FOV), which should yield 0.4 mm spatial resolution. Rapid data acquisition (2 μs/point giving a 1 ms data collection) resolves the boundaries of the straps accurately (top left). With 4 μs/point sampling giving a data collection of 2 ms duration, there is some slight blurring (top right). With 8 μs/point and a data collection of 4 ms, blurring becomes obvious (bottom left) and with 16 μs/point and 8 ms data collection, blurring is so marked that the internal boundaries are hardly resolved at all.

The loss of definition is due to the rapid decay of the signal from the rubber straps during the data collection. This is minimal for shorter data acquisition times (e.g., when the acquisition is of 1 ms duration and thus only slightly greater than the 0.8 ms $T_2$ of the straps, but is obvious for a data acquisition time of 8 ms (approximately ten times longer than the $T_2$ of the straps).

The distinction between $T_2$ and $T_2^*$ is significant in this context. $T_2$ is the spin-spin relaxation time and is a fundamental property of tissue (at a specific field strength, temperature etc.). It may be measured (for example) with a Carr-Purcell-Meiboom-Gill sequence, using a series of phase alternated inversion pulses. The measurement may, within fairly broad limits, give values of $T_2$ largely independent of the measurement technique.

On the other hand, $T_2^*$ is the relaxation time observed with a gradient echo pulse sequence. $T_2^*$ includes both $T_2$ relaxation and coherent dephasing effects, which are generally highly dependent on the imaging technique used. These dephasing effects arise from spins within a voxel (a volume element) that have different precessional frequencies. The difference in frequency is affected by voxel dimensions, including slice thickness. In general, the larger the voxel, the greater the field inhomogeneity within it, and the greater the dephasing effect. Specification of $T_2^*$ thus requires a knowledge of voxel size and field inhomogeneity within it.

The difference between $T_2$ and $T_2^*$ may be reduced if TE is decreased. For example, decreasing TE from a value of about 10 ms to about 0.1 ms or less may significantly reduce the difference between T2 and $T_2^*$. Dephasing effects due to (for example) poor shimming or inhomogeneity in large voxels at air-tissue interfaces may be reduced.

When imaging particular tissue using a gradient echo sequence type, it may be difficult or impossible to ascertain whether changes in $T_2$ or $T_2^*$ are being observed, in the absence of additional information. In tissues that are known to contain no dephasing sources it may be reasonable to assume that the measurement essentially reflects $T_2$. In other tissues (for example cortical bone), that assumption may not be accurate, since dephasing effects may be affecting the signal even at ultra-short TE's.

Magnetization transfer in clinical MR imaging can be used to provide access to the otherwise undetectable short $T_2$ components in tissue. By applying off-resonance RF pulses it is possible to saturate the short $T_2$ (broad line) components while leaving the long $T_2$ (narrow line) components unaffected, and to detect the effect of this saturation through the exchange that occurs between the otherwise undetectable short $T_2$ components and the detectable long $T_2$ components which are imaged. This indirect technique for imaging of short $T_2$ components has advantages over conventional techniques in applications such as detecting abnormalities in normal-appearing white matter. The technique is applicable to tissues with a minority of short $T_2$ components (since they also have long $T_2$ components which provide the detectable signal) and to tissues where the short and long $T_2$ components are in exchange. Magnetization transfer can provide indirect access to very short $T_2$ components (e.g. with $T_2$'s of about 1-10 μs) which may not be directly detectable with UTE imaging.

To put clinical MR system performances in context, it is worth noting the performance of imaging spectrometers used for solid state studies on small samples (milligrams or grams) with very short $T_2$'s. Typically these systems utilize short RF pulses (e.g., about 1-2 μs duration) with high peak power, a broad bandwidth and rectangular pulse profiles. The spectrometer can switch very rapidly from transmit to receive mode (e.g. in about 1 μs or less), so signal loss due to the rapid decay of short $T_2$ components is minimized. Available gradient strengths (over a very small field of view) are much higher and rise times much shorter than those on clinical systems. In addition, $B_0$'s are usually higher providing a greater signal to noise ratio. Biological safety issues are not a concern with inanimate samples.

In comparison, when examining humans (with masses on the order of kilograms) on clinical MR systems, transmitter coils are large, and $B_1$ power limitations generally mean that the shortest RF pulses are of the order of 0.25 to 0.40 ms in duration (depending on flip angle). This value is similar to that of the $T_2$ of tissues such as cortical bone as well as that of the short $T_2$ components in other tissues.

Most clinical MR systems are used primarily to image long $T_2$ components. Thus, there has been no particular demand for rapid switching from transmit to receive mode. Typical minimum switching times are of the order of about 0.08 ms to about 0.10 ms. These switching times are long enough to allow generally highly resonant transmitter coils time to ring down. However, a significant proportion of the signal from short $T_2$ components may be lost with switching times of these magnitudes.

Gradient performance, first to ramp the gradients up, and then to maintain them at a high amplitude is of importance when imaging tissues or tissue components with short $T_2$'s. As a general rule, the duration of useful data collection for a short $T_2$ component is of the order of $T_2$, or twice $T_2$. If gradient performance is limited both in slew rate and maximum strength, a significant proportion of the short $T_2$ signal may be lost before it can be spatially encoded.

With conventional 2DFT imaging, there is a delay after the initial RP excitation when the slice selection gradient is used to re-phase the signal. Time is also required for the phase encoding pulses, the initial dephasing lobe of the frequency encoding pulse, and the first half of the data acquisition before the center of k-space is reached. The term 2DFT is used to describe rectilinear mapping of k-space, such as that described above with reference to FIG. 1C. 2DFT is also known as phase-frequency encoding or spin-warp imaging, although both this method and UTE sequences such as sequence 200 of FIG. 2A use 2D Fourier transforms to reconstruct the image (after the data has been re-gridded, in the case of UTE imaging).

It is possible to avoid the need for rephasing of the slice selective RF excitation pulse by first collecting the data with the slice selection gradient in one direction and adding this to data collected in the same way with the slice selection gradient reversed, as described above and shown in FIGS. 2A to 2C. At the end of this process the signal is effectively in-phase and data sampling can, in principle, begin as soon as the RF pulse and the slice selection gradient are ramped down to zero. The use of radial imaging of k-space with the acquisition starting in the center of k-space (where no gradient is required for the initial encoding) means that there is no need for a phase-encoding gradient, a read-dephasing gradient, or additional time to get back to the center of k-space in the read direction.

Additionally, data sampling can continue while the gradient is being ramped up (although sampling during ramping takes a longer time than when the gradient is fully ramped up, by a factor of about two) as well as after the gradient has reached its plateau. The gradient also needs to be ramped down very quickly at end of the RF excitation since persistence of the gradient after the end of the RF pulse may result in dephasing of the signal.

It is usual to take TE as the time from the mid-point of the RF excitation pulse to that of the sampling of the center point of k-space. This is appropriate (or only slightly in error) for long $T_2$ components, but the precise value of TE may become uncertain with short $T_2$ components. The effectiveness of the RF pulse is biased towards the end of excitation for short $T_2$ components so the end point of the RF excitation may be more appropriate to use as the time origin for TE.

The pulse sequence shown in FIG. 2A is not a spin echo or gradient recalled echo (since reversed gradients are not used to form an echo). The pulse sequence detects the free induction decay (FID) directly. There is no echo since the signal is not refocused and each half excitation is not fully rephased. It is only after they are added that the k space data is in phase. Echoes are formed with most types of clinical imaging and for simplicity it is usual to regard the UTE sequence as a type of gradient echo.

While simple UTE sequences are effective for imaging tissues with a majority of short $T_2$ components, some form of long $T_2$ component reduction may be used to selectively image short $T_2$ components in tissues in which they are a minority.

One method that may be used to reduce signal contributions from longer $T_2$ components is to use a long (e.g. 10 ms) rectangular 90° pulse followed by a dephasing gradient, as outlined above. Another method involves the use of an initial long inversion preparation pulse (e.g. about 4 ms) to selectively invert long $T_2$ components followed by a TI chosen to null them. This technique requires at least some knowledge of the $T_1$ of the long $T_2$ components. Comparison with the same procedure but making use of a short inversion pulse (e.g. about 0.40 ms) in an attempt to simultaneously invert both long and short components provides a measure of the effectiveness of the technique.

Figure 10A:
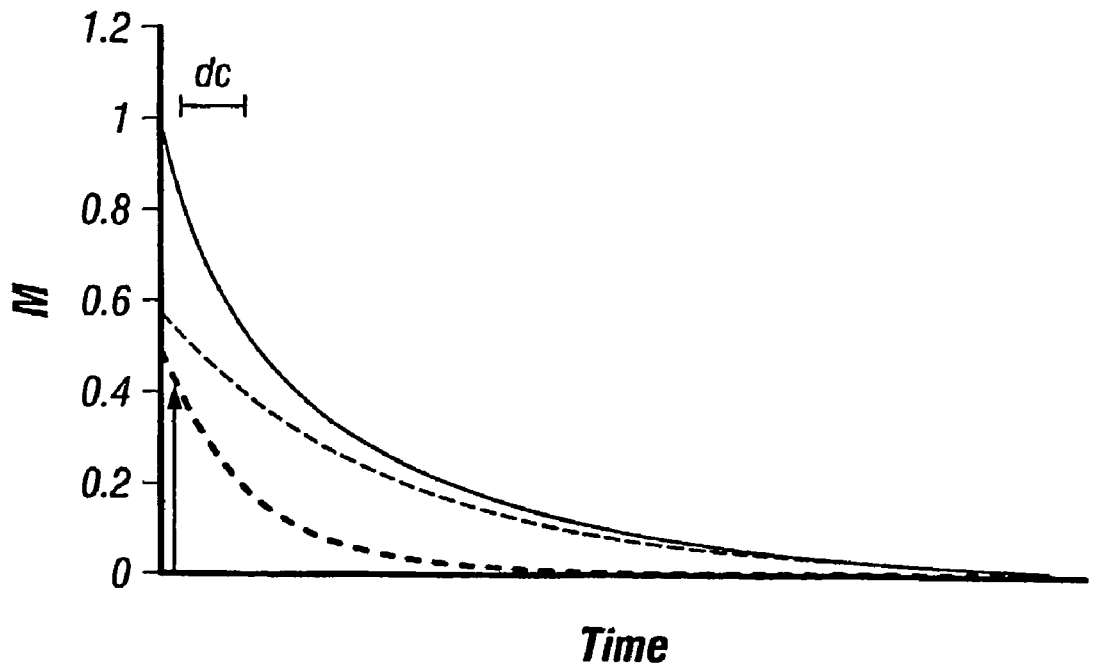
FIG. 10A shows magnetization for a pulse sequence incorporating long $T_2$ signal reduction.

FIG. 10A illustrates the effectiveness of these methods for signal suppression of longer $T_2$ components. The total magnetization is shown as a continuous line, the short $T_2$ components as circles and the long $T_2$ components as dashes. Reduction of the long $T_2$ components in reduces the detectable magnetization to that from the short $T_2$ components (vertical arrow).

Figure 10B:
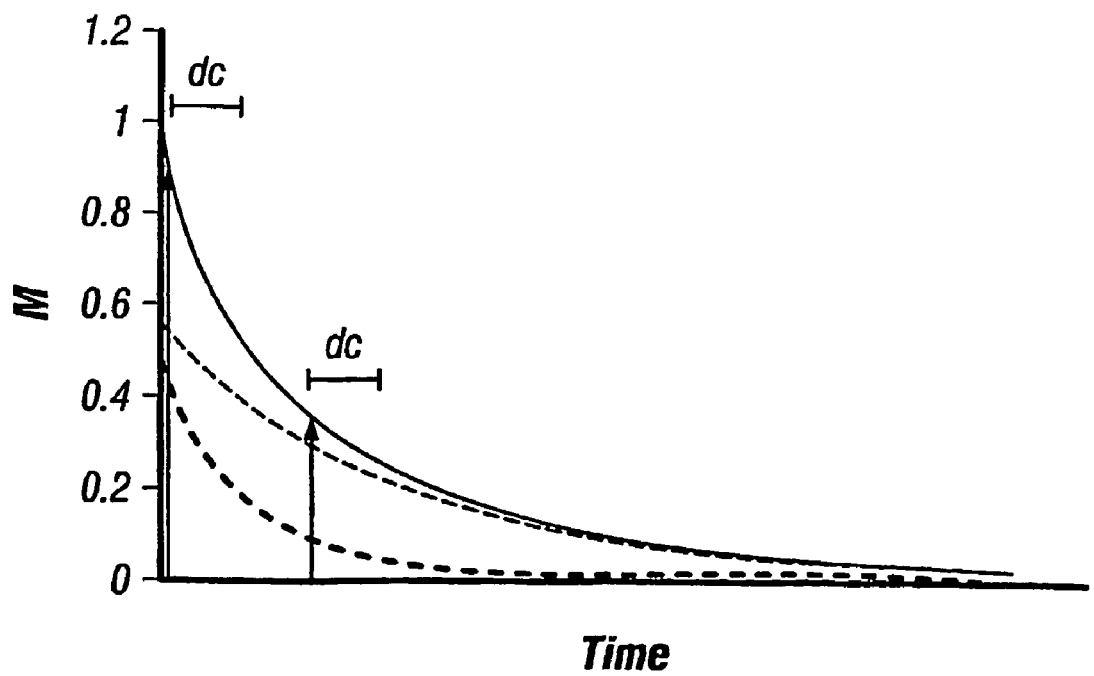
FIG. 10B shows magnetization for a different pulse sequence incorporating long $T_2$ signal reduction.

A third method is to subtract a later echo image from the first (UTE) one and produce a difference image. Tissues or fluids with a long $T_2$ have their signal attenuated by this procedure, while tissues which have a short $T_2$ and decay rapidly between the two echoes are highlighted on the resulting difference image. FIG. 10B illustrates the effectiveness of this method for signal suppression of longer $T_2$ components. Again, the total magnetization is shown as a continuous line, the short $T_2$ components as circles and the long $T_2$ components as dashes. The subtraction of the second echo from the first produces a difference image, in which most of the signal comes from the short $T_2$ components, since they decay rapidly between the two echoes.

Pulse sequences employing half RF pulses and radial sampling have been applied to lung imaging. This implementation incorporated spectroscopic imaging and a modified Dixon technique for separation of fat and water signals as well as a 90° rectangular preparation pulse for suppression of long $T_2$ components. Pulse sequences with half RF excitations and center out radial mapping of k-space with TE's of about 0.07 to about 0.08 ms have been implemented, but in a more modular form. This is discussed more fully below.

Truncated RF pulses of with durations from about 0.40 to 0.50 ms may be used with slice selective gradients applied in one direction and then reversed for the second half of the acquisition. The two sets of data are added to give a single radial line of k-space, and the process is repeated through 360° in 128-512 steps. The data is mapped onto a 512×512 grid and reconstructed by 2D Fourier transformation to give a gradient echo type of image. In some implementations, four sets of images with typical TE's of 0.08, 2.87, 5.66 and 8.45 ms (at 2 µs per analog to digital converter [ADC] sample) or 0.08, 5.95, 11.08 and 17.70 ms (at 4 µs per ADC sample) are obtained. The length of the ADC sample point during the acquisition represents a compromise between (at 2 µs) acquiring data before the signal had significantly decayed (but at a wide bandwidth which decreased signal to noise ratio), and (at 4 µs) acquiring data for longer which allows the signal to decay further (but with a narrower bandwidth and hence increased signal to noise ratio). In some implementations, data is usually sampled over 256-512 points.

Slice selection in multislice sets is performed with sequential excitations with the positive gradient, followed by sequential excitations with the negative gradient. Multislice interleaved excitations may interfere directly with the half RF pulse, since the slice profile of a half pulse alone is spread out.

Versions of the basic sequence with frequency based fat suppression and/or long $T_2$ component suppression have been implemented. Initial short (0.40 ms) and long (4 ms) inversion pulses are used as preparation pulses. With each variant of the sequence, difference images formed by subtraction of subsequent echo images from the first echo image are produced. Fields of view of 12-40 cm are employed with slice thicknesses of 4-8 mm. 2-20 multiple interleaved slices are obtained. TR's of about 500 ms are commonly used with CUTE and FUTE sequences with flip angles (for long $T_2$ components) of 45-80° and slice gaps of 10-100%. Serial studies of contrast uptake use a TR of 50-100 ms. Inversion recovery sequences had TR's of 650-2500 ms. Breathold and cardiac gated sequences use TR's of 10 ms. Scan time varied from 12.8 s to 17 minutes. Studies were performed on Sonata 1.5T systems (Siemens, Erlangen).

To measure $T_1$ values in short $T_2$ species (e.g. for cortical bone) a saturation pulse was used with a series of saturation recovery delays (TSR) prior to excitation and acquisition. Analysis involved the placement of regions of interest within the tissues, subtraction of the signal from long $T_2$ components and fitting of the resulting intensity versus TSR curves to a saturation recovery model.

To measure $T_2^*$ values (e.g. for cortical bone) TE's for the first echo of 0.14, 0.30, 0.46, 0.78, 1.10, 1.52, 1.94, 2.46 ms were used with a TR of 500 ms. Analysis involved placement of regions of interest and fitting the resulting intensity versus TE curves to an exponential decay with an offset (due to the presence of small concentrations of long $T_2$ components).

To summarize, several notable features of UTE sequences are listed below:

Preparation pulses: With UTE sequences, preparation pulses similar to conventional pulses may be used, but inversion pulses may only effect long $T_2$ components. Long inversion pulses can be used for nulling of these $T_2$ components. Magnetization transfer pulses may directly saturate short $T_2$ components and diminish their signal. Fat saturation and multiple slice multiple echo imaging may do the same.

RF excitation and slice selection: for short $T_2$ components, RF excitation is short, and usually less than the $T_2$ of the components of interest. The RF pulse may be truncated. Slice selection may be achieved in two halves with reversed gradients, to avoid the need for a rephasing gradient lobe. Data acquisition may begin as soon as each half of the slice selection is completed, within limits that may be posed by RF switching times.

Mapping of k-space: Radial mapping from the center of k-space is performed (without phase encoding pulses), including acquisition during the ramping up of the gradient. This should be completed in a time of the order of the $T_2$ of the tissue of interest. Data acquisition is generally performed at wide bandwidth.

Post acquisition: Subtraction of later echoes from the first may be used to selectively reduce the signal from long $T_2$ components.

In some implementations, contrast agents may be used. For example, intravenous Gadolinium chelates (e.g. Gadodiamide 0.3 mmol/kg) may show enhancement in tissues when imaging tissues with short $T_2$'s using UTE sequences. Using conventional sequences, no appreciable signal from the short $T_2$ signal may be detected, either before or after contrast administration. However, administration of the contrast agents may be effective with UTE sequences, due to a reduction of $T_1$. The use of such contrast agents (and/or other methods of reducing $T_1$) may be of particular interest because some tissues with a majority of short $T_2$ components are avascular or relatively avascular. Contrast enhancement may thus allow solute transport or perfusion to be studied. The detection of normal enhancement in tissues with short $T_2$'s may allow a reduction in this enhancement to be recognized in disease (see discussion below, and FIGS. 17A and 17B). Even in tissues where signals are detectable with conventional sequences, the signals from the majority of longer $T_2$ tissues may be detected earlier during their decay, and signal from the minority of short $T_2$ components may also be detected. This may allow the tissue to be visualized with a higher signal intensity before enhancement and to show a greater increase in signal after enhancement (see discussion below, and FIGS. 15A and 15B).

Another feature of interest with UTE sequences is that UTE sequences may be able to detect signals from tissues with short $T_2$'s and concurrently reduce or suppress signals from tissues or fluids with a long $T_2$'s. This can be achieved by the use of different long $T_2$ reduction techniques. This option may be useful with contrast enhancement with Gadolinium chelates where frequently the greatest change is seen in blood (which has a long $T_2$) but the area of most clinical interest may be adjacent or associated tissue with a short $T_2$ (see discussion below and FIG. 13).

Magnetic iron oxide particles (MIOP's) typically produce a loss of signal through susceptibility effects. This loss of signal may not be manifest with conventional sequences in tissues which produce no signal prior to enhancement such as tendons and ligaments. In this situation, the presence of these particles may be inferred by loss of signal in surrounding tissues or fluids which have detectable MR signals. The use of UTE sequences to produce a detectable signal in the tissues of interest may provide a baseline to recognize a reduction in this signal produced by MIOP's.

A particular problem with intravenous use of MIOP's is that MIOP's frequently produce a loss of signal in the area of most interest, which may make image interpretation difficult. (Gadolinium chelates, as most commonly used clinically, do the reverse, by increasing the signal in the area of most interest). Also, with the use of oral MIOP's to reduce the unwanted signal from bowel contents, the loss of signal may extend beyond bowel and produce loss of signal in adjacent organs.

UTE images typically show low sensitivity to susceptibility effects but later echo images show higher sensitivity to these effects. Subtraction of a subsequent echo from the first produces a difference image in which the anatomic detail from the first (UTE) image is well preserved but modulated by the susceptibility dependent contrast developed by the later echo, with higher signal on the difference image representing a greater degree of susceptibility effect.

The interpretation of UTE images follows established principles, but there are some interesting differences. The term "$T_2$ weighted" as usually applied to a pulse sequence is generally taken to mean weighting for long $T_2$, components in a tissue or fluid by use of a long TR and long TE. Sequences may also be $T_2$ weighted, but for short $T_2$ components (e.g. with $T_2$'s less than 10 ms), using short TE's rather than long ones. For clarity, in situations where there may be confusion, it may be necessary to use the terms "long $T_2$ weighted" and "short $T_2$ weighted". Sequences may be both short $T_2$ and $T_1$ weighted at the same time if they have a short TE and a short TR, or just short $T_2$ weighted if they have a short TE and long TR (relative to $T_1$).

The $T_2$ weighting of a sequence is maximal for small increases or decreases in the $T_2$ of a tissue when its TE is about the same as the tissue $T_2$. So UTE sequences alone (e.g. TE=0.08 ms) are not particularly $T_2$ weighted for most tissues in the short $T_2$ range since these tissues often have longer $T_2$'s. Although the $T_2$ weighting of UTE sequences is low for most short $T_2$ tissues, $T_2$ weighting increases for tissues in the short $T_2$ range with later echoes (e.g., with TE=2.87, 5.66 and 8.45 ms). These may detect an increase or decrease in signal intensity in disease relative to normal tissue.

The long $T_2$ reduction techniques also affect $T_2$ weighting, but in a different way. They selectively attenuate the signal from tissues with long $T_2$'s, leaving the signal from short $T_2$ components. As a result, the sequence only shows signal from tissues with $T_2$'s within a restricted range or window.

Tissues may enter or leave this window of visibility at either end by increasing or decreasing their $T_2$'s. The width of the window varies with the duration of the rectangular pulse, the length of the nulling inversion pulse, or the TE of the subtracted echo. Within the window the above consideration about the choice of TE in relation to $T_2$ apply. The situation may be complicated by tissues having two or more components in the short $T_2$ range present in significant concentrations.

Figure 11:
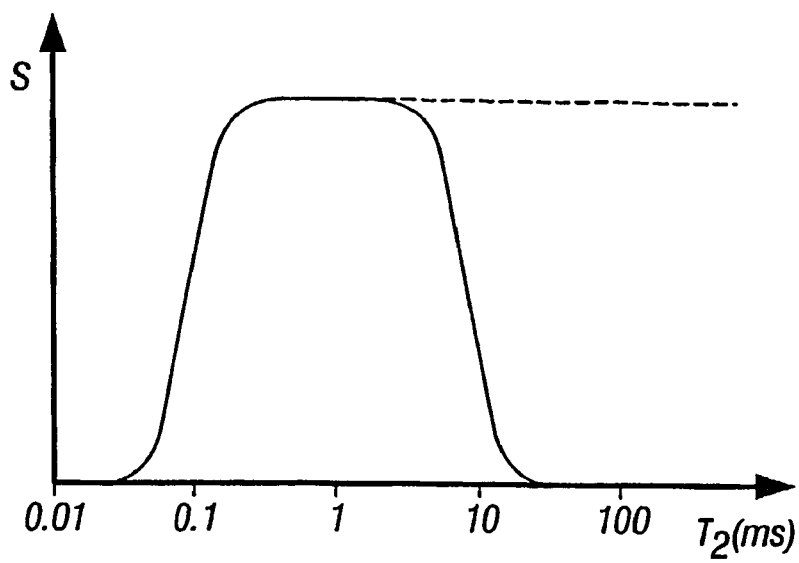
FIG. 11 is a stylized sensitivity profile of an ultra-short TE sequence.

FIG. 11 illustrates this effect. FIG. 11 is a stylised sensitivity (S) profile of a UTE sequence to tissues with different $T_2$'s, shown on a logarithmic scale. The lower cut off point was set by machine performance, and is probably between 0.01 and 0.1 ms. Without $T_2$ reduction, the sequence is sensitive to $T_2$ components in the range of 1-10 ms and higher (dashed line). With $T_2$ reduction techniques, the sensitivity to longer $T_2$'s is reduced to zero (continuous line). There is thus a window of short $T_2$'s which UTE sequences with long $T_2$ reduction techniques are sensitive to. Tissues can enter or leave this window of visibility by increasing or decreasing their $T_2$'s. Note that the graph does not take into account differences in concentration of $T_2$ species, or the effects of $T_1$. Both of these factors affect the detectable signal.

UTE sequences are $T_1$ weighted if the TR for CUTE, FUTE, LUTE and FLUTE sequences is about the $T_1$ of the tissue of interest, with due allowance for flip angle. This is a common situation. With inversion recovery sequences, $T_1$ weighting is maximal if the TI is about the $T_1$ of interest. Cortical bone has a $T_1$ in young and middle-aged subjects of 130-160 ms at 1.5T, which is shorter than subcutaneous fat. The $T_1$ of cortical bone increases significantly with age to 260-280 ms in the ninth decade. Tendons, ligaments and menisci have relatively short $T_1$'s in the range of 300-600 ms at 1.5T. $T_1$'s of short $T_2$ components in tissues in which they are in a minority are less well characterized but are probably similar.

Conventional proton density weighted pulse sequences with typical TR's of about 2000-3000 ms and TE's of about 10-20 ms do not detect a number of short $T_2$ components which contribute to proton density as measured by chemical assay. Even UTE sequences may not detect extremely short $T_2$ components (although these components may be imaged using magnetization transfer, as outlined above). However, changes in proton density may be a greater source of contrast when imaging with short $T_2$ components than is the case with long $T_2$ components.

With inversion recovery sequences, the use of a long initial inversion pulse may mean that long $T_2$ components may experience an inversion recovery sequence, while short $T_2$ components experience a partial saturation type of sequence since they do not experience the inversion pulse. Thus, with long TR's, short $T_2$ components may be fully recovered while long $T_2$ components may still be recovering their longitudinal magnetization after the inversion pulse.

Each of the long $T_2$ reduction techniques has advantages and disadvantages. Long $T_2$ component suppression with a long preceding 90° pulse and dephasing has the disadvantage that no unsuppressed image is available, but the advantage that susceptibility effects are not introduced by subtraction of a later echo. However, susceptibility effects may render the long narrow bandwidth pulse ineffective, and result in high unsuppressed signal from long $T_2$ components. The long inversion pulse sequences with nulling of long $T_1$ components may be difficult to interpret, due to magnitude processing and concerns about whether the chosen TI is correct. Subtraction images generally increase the noise level and introduce susceptibility effects, but both the original images and the subtracted image are available for examination.

With LUTE, FLUTE and 1 STUTE sequences, comparison of the first and subsequent echo signal intensities using difference images provides a measure of the success of the long $T_2$ reduction technique. If there is considerable reduction of signal between the two echoes then what is being imaged is mainly short $T_2$ components.

Changes induced by susceptibility effects may be obvious on later echo images and may not require subtraction from the first UTE to make them obvious if they are seen against a uniform tissue background. Subtraction may be more useful at interfaces and other regions where there is complex anatomy (e.g. with meninges and blood vessel walls), or where it may be desired to visualize short $T_2$ components without confounding effects from tissues or fluids with long $T_2$'s such as contrast enhanced blood.

To selectively show short $T_2$ components, subtraction images need to have adequate signal to noise ratio. Thus, cortical bone may be obvious in a subtraction image when it is situated close to a surface coil, but be of low signal on all sequences (including subtraction images) when examined at some distance away from the conductors of a body coil.

When double inversion recovery pulses ("black blood pulses") are used to reduce the signal from blood, the two inversion pulses may saturate the signal from short $T_2$ components in vessel walls.

Magic angle effects in tendons and ligaments are manifest as a relatively increased in signal on later echo images (due to the longer $T_2$) and a decrease in signal on difference images. These can be seen in the anterior cruciate ligament (ACL), on the femoral side of the posterior cruciate ligament (PCL) as well as at other sites.

The conspicuity of increased or decreased signal from short $T_2$ components within a tissue differs, depending on whether these components are in a tissue with a majority of short $T_2$ components or in a tissue with a minority of short $T_2$ components where the effect may be diluted unless the signal from the signal from long $T_2$ component is reduced. Likewise, the effect of a $T_2$ shortening process may be more obvious in a tissue with a minority of short $T_2$ components than in one with a majority where there are no long $T_2$ components available in the tissue to have their $T_2$ reduced.

Even when it is not necessary to reduce the signal from long $T_2$ components in a tissue of interest with a majority of short $T_2$ components to visualize them (e.g. tendons, ligaments), it may still be useful to do this in order to increase the conspicuity of these tissues by reducing the signal from other tissues with a minority of short $T_2$ components.

Diseases which increase the $T_2$ of tissues with a majority of short $T_2$ components may render them more obvious on later echo images but less obvious on difference images (i.e. the increase in $T_2$ takes them outside the visible window in FIG. 11). With conventional pulse sequences, contrast enhancement in these tissues (e.g. tendons and ligaments) may only be recognizable in areas where the $T_2$ is increased so that signal is detectable. Paradoxically, with difference images, these may be just the areas where contrast enhancement is not visible on difference images, because the increased $T_2$ leads to attenuation of the signal.

Tissues with long $T_2$'s but short $T_2^*$'s are common at tissue-air interfaces. Susceptibility effects affecting the mucosa of the nasal sinuses are obvious with later echoes and on difference images. Fatty bone marrow within trabecular bone contain significant short $T_2^*$ components. Large bowel contents typically have a short $T_2$ and/or $T_2^*$ and display a high signal on UTE and difference images derived from them. The signal at the lung bases on subtraction images seen in normal volunteers probably represents a short $T_2^*$ effect due to susceptibility effects either from fluid in lung or blood. Lung has short $T_2$ components as well as short $T_2^*$ components.

Particular artifacts associated with the use of UTE sequences include radial lines, susceptibility effects, out-of-slice effects, flow dephasing effects and effects due to delayed RF switching. Radial artifacts resemble those seen with cat scans (CT). Susceptibility artifacts may be manifest as high signal on difference images. However, within cortical bone they may produce a relative increase in signal on late echo images and have a low signal (rather than a high signal) within the bone on difference images.

Out-of-slice artifacts can produce high signal at boundaries or interfaces. Materials with short $T_2$'s in the receiver coils often have a high signal. Plastic inter-uterine contraceptive devices (IUCD's) also have a high signal, as do various items of clothing. Bone may be diamagnetic to a different degree than other tissues and this may result in phase cancellation at boundaries. Large artifactual changes on difference images can arise from subtraction of later out-of-phase (fat and water protons) echo images from the first (UTE) image. Motion artifact is generally more prominent with later echoes, and generally becomes more obvious on difference images. Flow of blood can lead to dephasing on the later echo images and a high signal on difference images which simulates signal from short $T_2$ components. Delay in coil switching and/or eddy currents may produce a mottled effect, and a relative reduction of the first echo compared with the second, with negative signals on difference images.

To date we have studied over 120 patients using the techniques described above. The selection of patient groups follows from a number of considerations. The detection of signal from tissues with short $T_2$'s which have previously been "invisible" provides a new range of conspicuity options as well as new anatomic detail which has previously been submerged in low tissue signal. Pathologic processes which might either increase or decrease the signal from short $T_2$ components (as outlined in section 2) have also provided a guide for the use of UTE sequences. Applications in which conventional imaging has been relatively unrewarding but in which magnetization transfer, MR spectroscopy or other imaging techniques have shown abnormalities have been another focus of attention.

The proton signal from cortical bone probably comes mainly from the organic matrix (principally collagen), bound water and some free water. It may provide different information than conventional radiological methods, which mainly reflect the calcium content of the mineral component. Serial scanning shows enhancement in normal cortical bone. After intravenous Gadodiamide there was a 23% increase in signal with a peak at about 10 minutes in the study illustrated.

Figure 12:
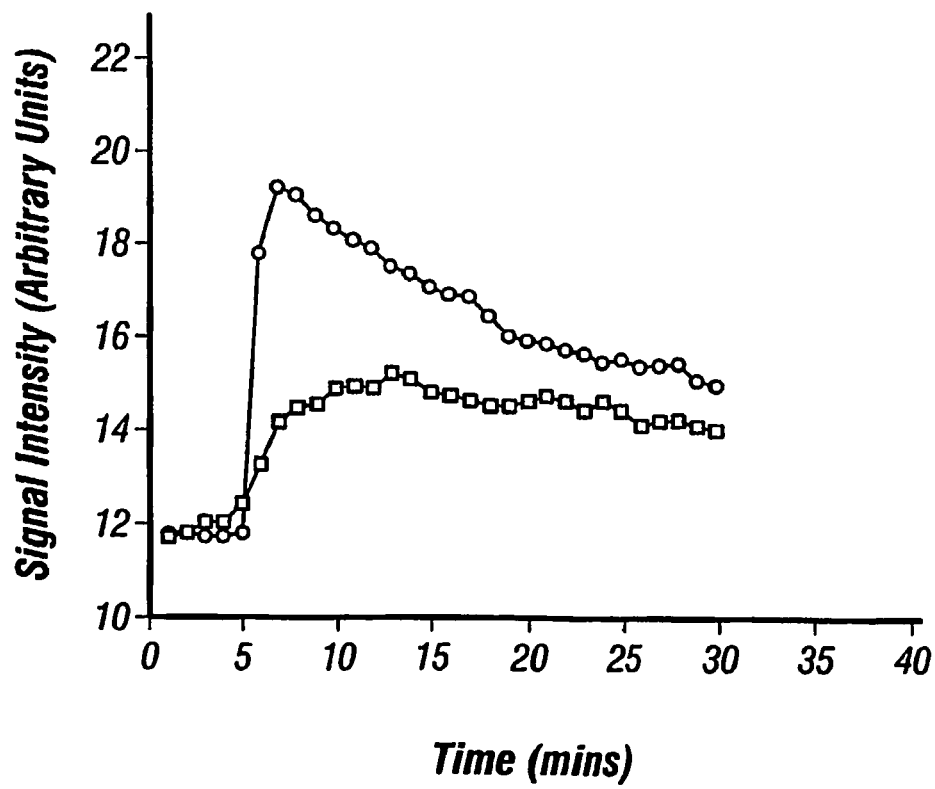
FIG. 12 is an image of cortical bone after fracture of the tibia.

FIG. 12 shows signal intensities in cortical bone after fracture of the tibia. Intravenous Gadodiamide was administered after five minutes. Results in one patient four days after fracture (squares), may be compared with those in another 3½ months after fracture (circles). There is a faster and higher increase in signal in the patient imaged 3½ months after his fracture.

Figure 13:
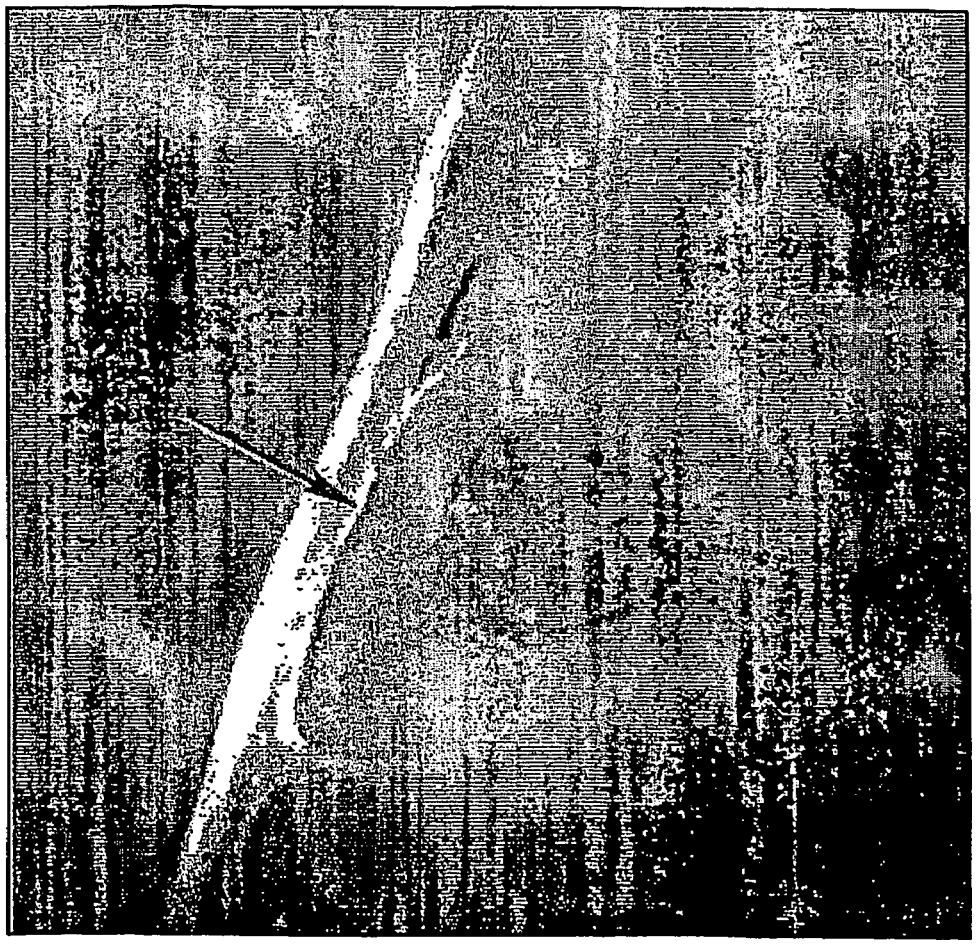
FIG. 13 is an image of a normal tibia.
Figure 14C:
Figure 14D:

The periosteum is well seen in many areas, although there may be other causes of high signal adjacent to cortical bone, and periosteum should to be differentiated from these. FIG. 13 shows a normal tibia, imaged using transverse d FUTE (TR/TE=500/0.08 minus 5.95 ms). The periosteum (arrow) is highlighted. Enhancement may be specifically demonstrated in the periosteum without the confounding effect of high signal from blood by the use of subtraction. FIGS. 14A to 14D show images of a fracture of the tibial plateau three days after injury. Coronal FUTE (TR/TE=500/0.08 ms) (FIG. 14A) and d FUTE (TR/TE=500/0.08 minus 5.95 ms) (FIG. 14B) images before enhancement and the same FUTE (FIG. 14C) and d FUTE (FIG. 14D) images after enhancement. The periosteum is just seen in FIG. 14B. Marked enhancement of blood vessels and other tissues is seen in FIG. 14C, but subtraction specifically shows the enhanced periosteum in FIG. 14D (arrows).

Figure 15B:
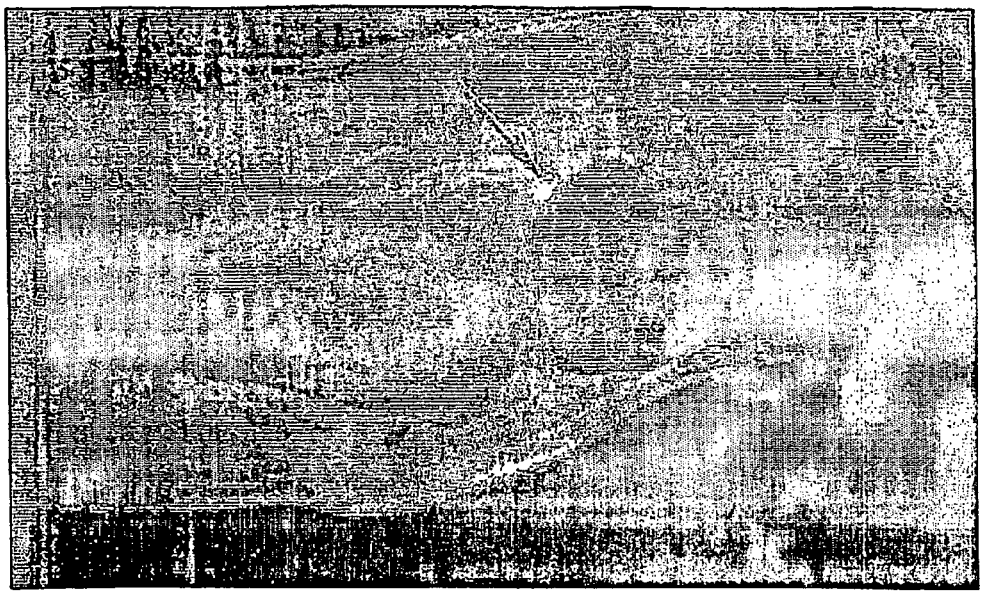
FIGS. 15A and 15B are images of the posterior cruciate ligament.
Figure 15A:
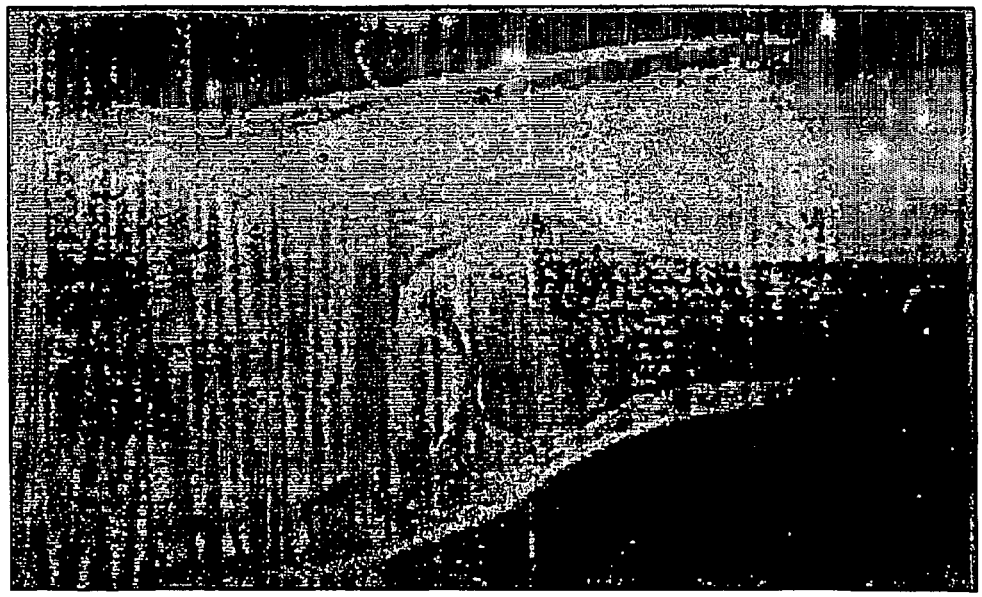

High signal was consistently seen in ligaments. Local enhancement may be seen after injury. FIGS. 15A and 15B are sagittal d FUTE (TR/TE=500/0.08 minus 11.08 ms) images of the posterior cruciate ligament (PCL) before (FIG. 15A) and after (FIG. 15B) enhancement. A focal area of enhancement is seen on the tibial side of the ligament (arrow).

Figure 16:
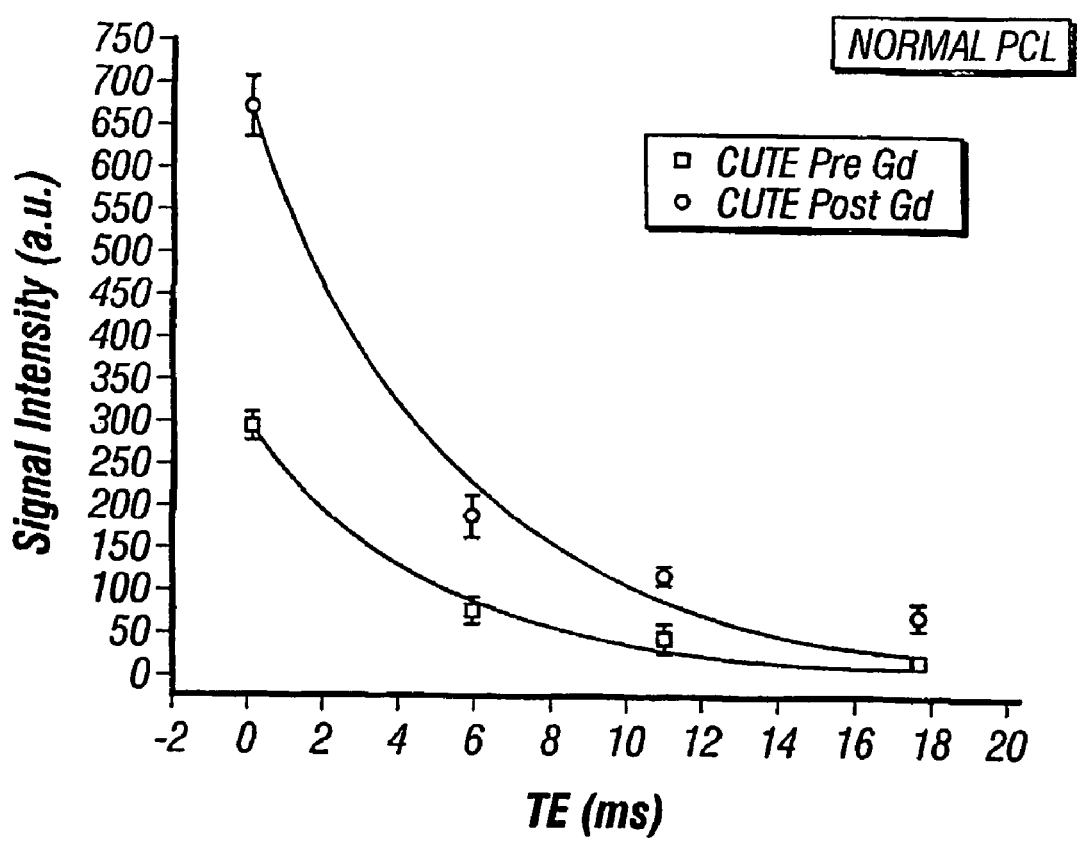
FIG. 16 is a plot of signal intensity versus TE for a normal posterior cruciate ligament.

FIG. 16 is a plot of signal intensity versus TE for the normal posterior cruciate ligament (PCL), before and after contrast enhancement. FIG. 16 shows that the highest baseline signal and the largest increase in signal are seen in this short $T_2$ tissue with the shortest TE. FIG. 16 was obtained using a CUTE sequence and subsequent echoes (TR/TE=500/0.08, 5.95, 11.08 and 17.70 ms) for a normal PCL before and after contrast enhancement. The PCL shows the highest pre-enhancement signal and the greatest increase in signal with the shortest TE (0.08 ms).

Figure 17A:
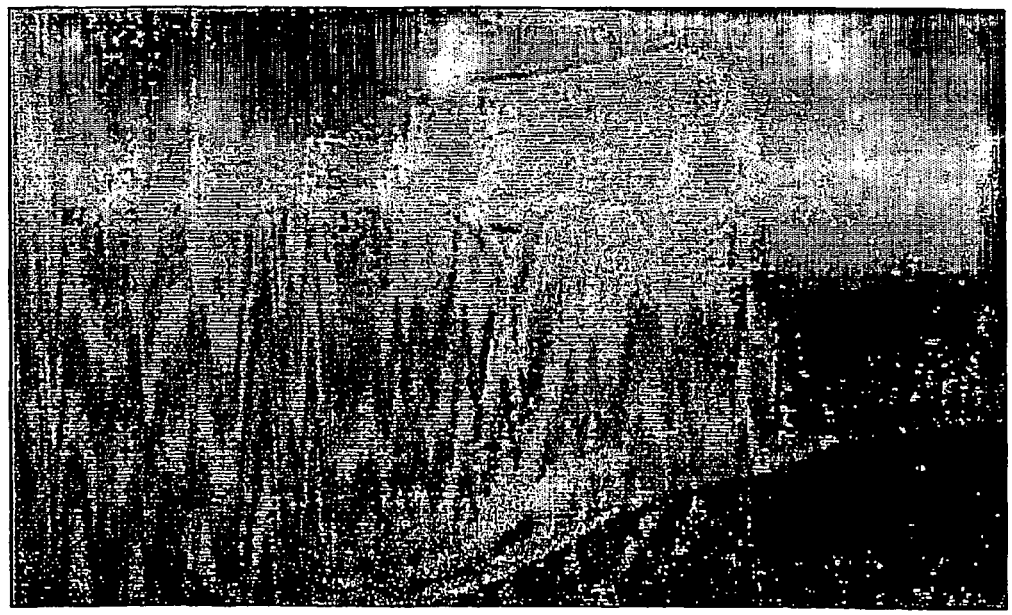
FIGS. 17A and 17B show the red zone of a meniscus.
Figure 17B:

The red (vascular) zone of the meniscus is well seen in FIGS. 17A and 17B. It has not been identifiable in previous studies in cadavers or patients. FIGS. 17A and 17B are sagittal d FUTE (TR/TE=0.08 minus 17.70 ms) images before (FIG. 17A) and after (FIG. 17B) enhancement. The red (vascular) zone of the meniscus is enhanced in FIG. 17B (arrows).

Figure 18A:
FIGS. 18A to 18C are images of a Achilles tendon.
Figure 18B:
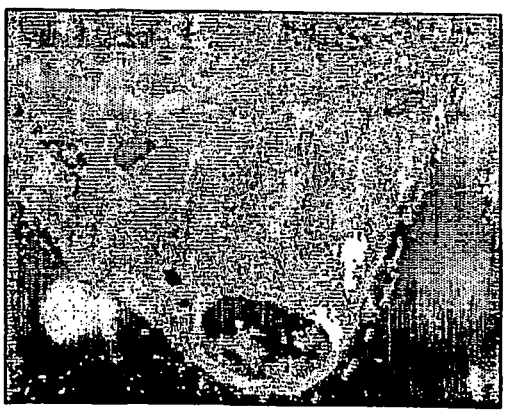
Figure 18C:

Regions of abnormality may be identified using the systems and techniques described herein. They may show less enhancement than that seen in normal tissue. This has not been possible previously in tissues in which normal enhancement could not be visualised. For example, FIGS. 18A to 18C are transverse CUTE (TR/TE=500/0.08 ms) images of the Achilles tendon after contrast enhancement (FIG. 18A), second echo (TR/TE=500/5.95) (FIG. 18B) and d CUTE (FIG. 18C) images formed from a subtraction of data for the image shown in FIG. 18B from the data for the image shown in FIG. 18A. The tendon shows two low signal areas in FIG. 18A and FIG. 18C. The smaller one has an increased $T_2$ on FIG. 18B but the other does not. The larger area has enhanced less than the surrounding normal tendon.

Figure 19:
FIG. 19 is an image of a liver.

In another example, the liver shows an increased signal on difference images in hemochromatosis, as shown in FIG. 19. FIG. 19 is a d FUTE image (TR/TE=500/0.08 minus 17.70 ms). With cirrhosis, there is a tendency towards an increase in $T_2^*$. The fibrosis present in this condition may be associated with inflammatory change and a long $T_2^*$ rather than the short $T_2^*$ seen in chronic "dry" fibrosis. There may also be a loss of endoplasmic reticulum and tightly bound water reducing the concentration of short $T_2$ components.

Figure 20:
FIG. 20 is an image showing tendons and muscle insertions in a pelvis.

FIG. 20 shows tendons and muscle insertions are highlighted in the pelvis. FIG. 20 is a d FUTE image (TR/TR=500/0.08 minus 5.95 ms). The strong signal may be from fibrocartilage.

Figure 21:
FIG. 21 is an image of a brain.

Short $T_2^*$ components can be seen in the normal white matter of the brain, as shown in FIG. 21. FIG. 21 is a dl STUTE image (TR/TE/TI=2500/0.08 minus 5.95/360 ms). In FIG. 21, the long $T_2$ components in the white matter have been nulled, leaving the short $T_2$ components (with a mean $T_2$ of about 3 ms) as high signal areas.

Figure 22B:
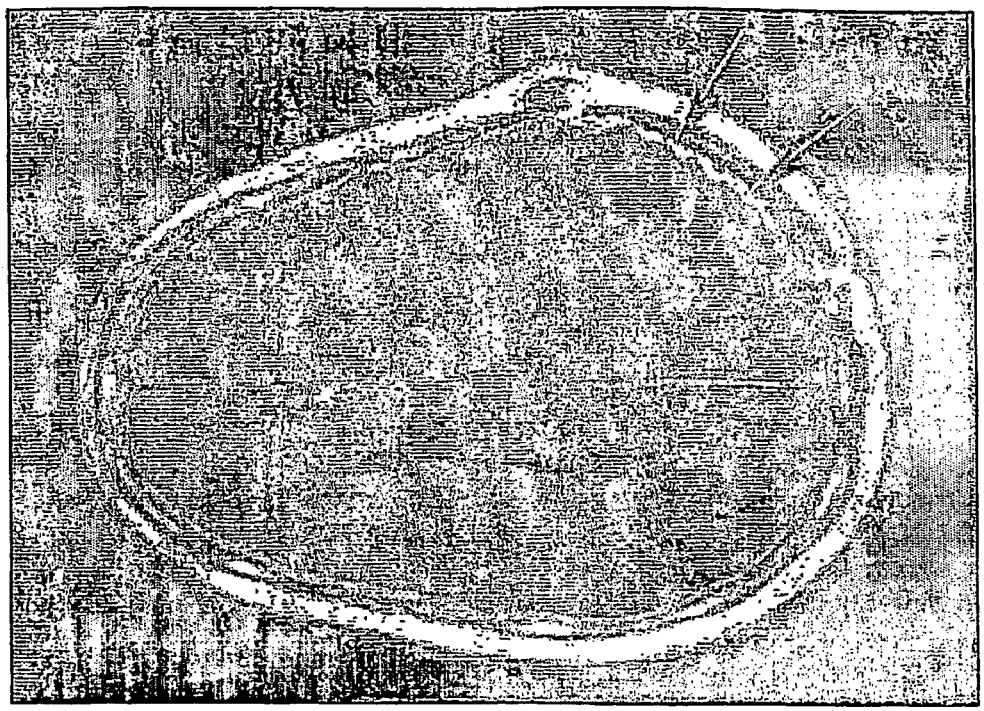
FIGS. 22A and 22B are images of a brain showing meningeal thickening.
Figure 22A:
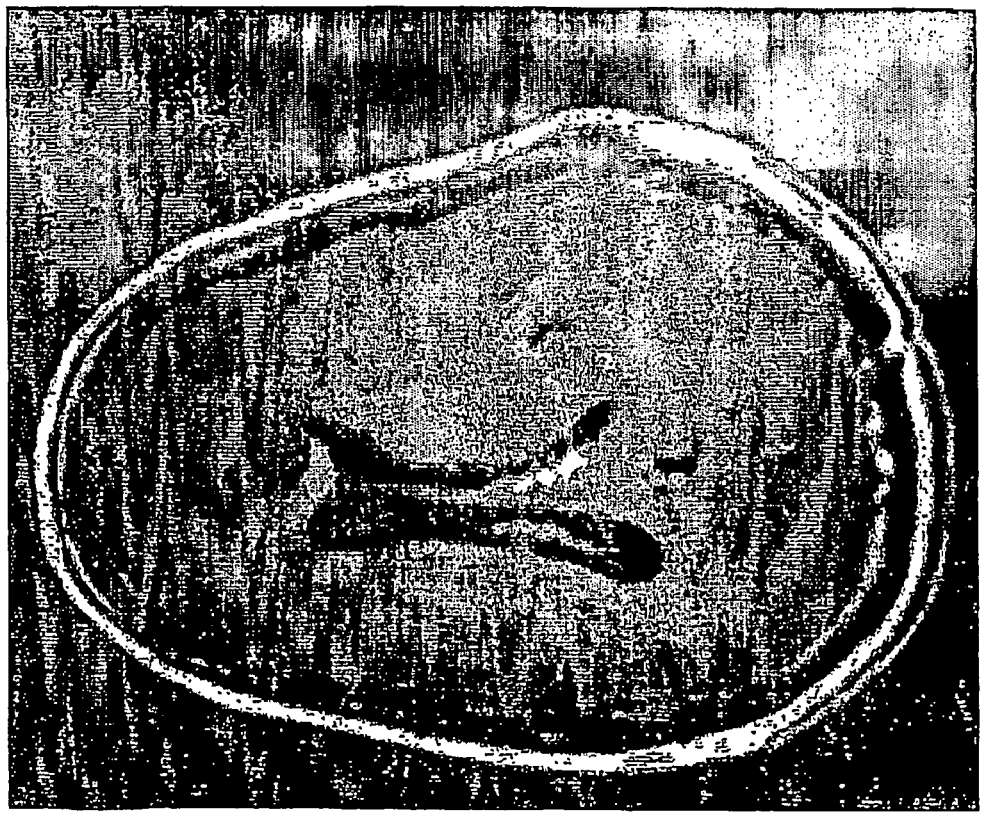

Applications in the brain have included conditions in which the signal from short $T_2^*$ components is increased such as angiomas, malignant melanomas, calcification and chronic gliosis as well as those in which it is decreased such as multiple sclerosis, many tumors, and vasogenic edema. Meningeal thickening is shown in FIGS. 22A and 22B. FIG. 22A is a conventional 2DFT $T_1$ weighted (TR/TE=500/8 ms) image, while FIG. 22B is a d CUTE (TR/TE=500/0.08 minus 5.95 ms) image. Normal meninges are well seen in FIG. 22B. There is thickening at the site of a previous craniotomy (arrows).

Cardiac imaging has been performed with adequate signal to noise ratio and scar tissue with a short $T_2^*$ has been identified as a high signal region on difference images.

Figure 23:
FIG. 23 is an image of a spine.

Imaging of the spine shows increased signal from ligaments and scar tissue and may show enhancement of abnormal interspinous ligaments. FIG. 23 is a sagittal contrast enhanced FUTE (TR/TE=500/0.08 ms) image, showing degenerative disease of the spine. Enhancement is seen in discs and scar tissue as well as the interspinous ligaments (arrows).

Figure 24B:
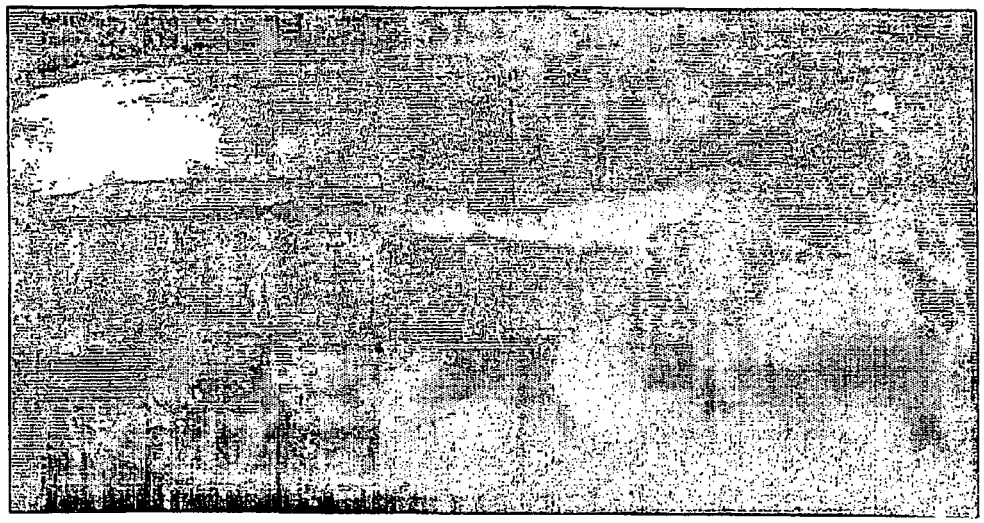
FIG. 24B is an image of a spine with thalassemia.
Figure 24A:
FIG. 24A is an image of a normal spine.

Thalassemia is of interest as a condition in which there is premature intervertebral disc degeneration in the lower thoracic and upper lumbar spine. High intensity bands can be seen parallel to the end plates with FLUTE sequences. These may be due to iron deposition shortening the $T_1$ and $T_2$ of the disc. FIG. 24A is a sagittal normal spine image obtained with a FLUTE sequence (TR/TE=500/0.08 ms), while FIG. 24B is an image of a patient with thalassemia obtained using the same sequence as that of FIG. 24A. High signal bands are seen parallel to the end plates within the discs on FIG. 24B.

Many other implementations are possible. Parameters, such as TR, flip angle and data sampling techniques for different tissue $T_1$'s and $T_2$'s may be optimized. Different and/or additional long $T_2$ signal reduction techniques may be used. In general, fast low flip angle techniques are likely to form the basic pattern for UTE imaging. The $T_1$'s of short $T_2$ components are generally short, which assists with fast sequences. The technique is also well suited to low flip angles, in order to keep RF pulse durations short.

Hardware may be used that optimizes $B_1$ power and reduces RF switching times, which may be inadequate for some coils (at TE of 0.08 ms). For example, MRI systems that provide for increased $B_1$ power and gradient strength with smaller dedicated transmit-receive coils and gradient sets for imaging of the brain, knee and other parts of the body may be used. These should allow shorter RF pulses and faster ramping to higher gradient strengths. For MR system hardware as a whole, it may be beneficial to provide a system capable of TE down to 20 μs or less, peak $B_1$ field of 30 μT or more, gradient slew rate of 200 T/m or faster, and gradient strength of 50 T/m or more.

3D acquisitions may be used to improve signal to noise ratio and for imaging complex structures such as articular cartilage and joints with thinner slices to minimise partial volume effects. Reversed radial sampling may improve the signal to noise ratio for later echoes. Gradient moment nulling is likely to be of value in reducing motion artifact from later echoes.

Spiral acquisitions also proceed from the center of k space and may provide more efficient coverage of k-space than radial sampling, although they generally take longer and this may lead to greater $T_2$ decay during data collection.

There may also be sequences in which the first "echo" is of the UTE type but later echoes use a conventional readout so that the sequence as a whole generates both types of image in a single acquisition. The combination of UTE gradient echoes and spin echoes for the later echoes would also remove some of the susceptibility artifacts that may be present with subtraction from the later gradient echoes. The radial approach is also compatible with partially parallel imaging techniques given adequate signal to noise ratio. This could allow faster imaging.

An interesting feature of some UTE sequences is that the center of k space is over-sampled so that the signal to noise ratio of low frequency components is higher than that of high frequency components. This may result in useful tissue contrast in particular clinical situations.

By combining UTE and magnetization transfer imaging, it may be possible to observe MT effects due to extremely short $T_2$ species (e.g. 10 μs) through their effects on short, but detectable $T_2$ species. Imaging of $T_1$ in the rotating frame involves the use of RF pulses for times of the duration of $T_2$ followed by conventional data collection. This may be achievable for short $T_2$ species using UTE sequences without exceeding rf power limitations (at least at low $B_0$ fields) and may be relevant for the study of the relaxation properties of large molecules with short $T_2$'s.

Most of this application has been concerned with imaging of tissues, but UTE sequences are also useful for imaging of blood flow, since short TE's decrease dephasing effects due to flow and can help preserve signal during turbulence.

Both phosphorus and sodium have tissue components with short $T_2$'s. These nuclei are present in lower concentration than protons but there are advantages to imaging them with UTE sequences. Radial acquisitions have been used to reduce the TE for sodium imaging to 0.3 to 0.4 ms. We have imaged sodium in tendons, ligaments and intervertebral discs using a TE of 0.07 ms and have also imaged phosphorus in cortical and trabecular bone.

Figure 25A:
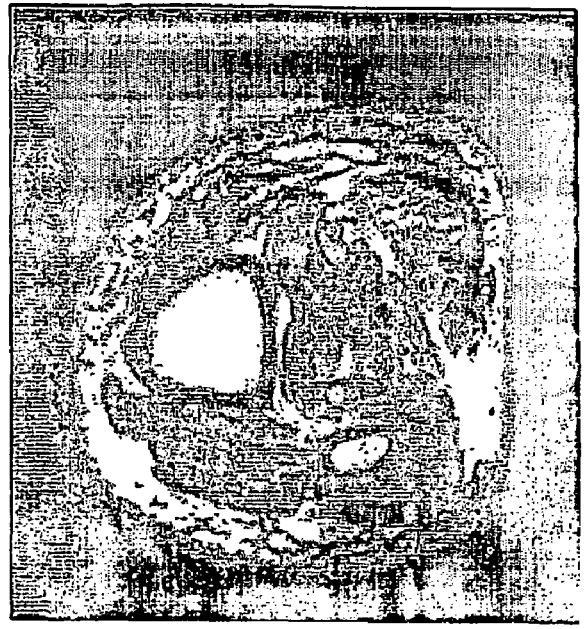
FIG. 25A is an image of a lower leg.
Figure 25B:
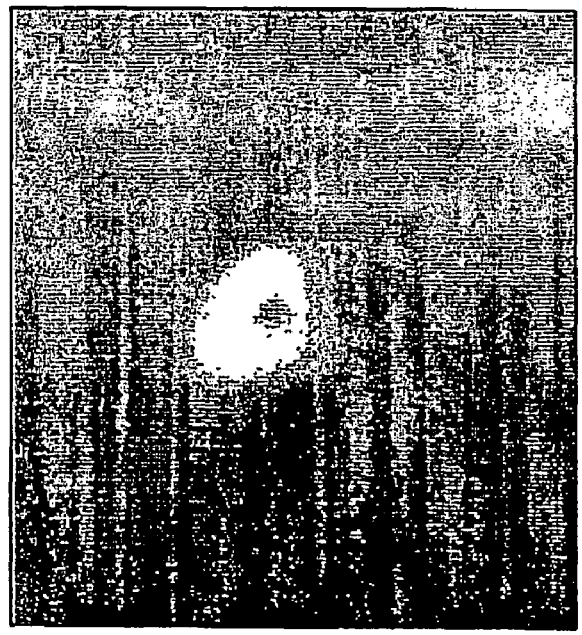
FIG. 25B is a phosphorus signal from the cortex of the tibia.

FIG. 25A is a transverse CUTE (TR/TE=100/0.07 ms) proton image of the lower leg, while FIG. 25B is a matching phosphorus image (TR/TE=300/0.07 ms) of the same region. Phosphorus signal is seen in the cortex of the tibia in FIG. 25B. The phosphorus in bone is in crystalline calcium phosphate and calcium hydroxy-appatite and has a $T_1$ of 10 s and $T_2$ of 0.17 ms at 1.5T. UTE CSI imaging has also been implemented for sodium and phosphorus studies of the heart.

In implementations, the above described techniques and their variations may be implemented as computer software instructions. Such instructions may be stored on one or more machine-readable storage media or devices and are executed by, e.g., one or more computer processors, or cause the machine, to perform the described functions and operations. For example, one or more controllers for an MRI system may perform functions according to computer program instructions.

A number of implementations have been described. Nevertheless, it will be understood that various modifications may be made without departing from the spirit and scope of the invention. For example, different pulse sequences may be used for UTE imagining. Additionally, different combinations of the above features may be used. Note also that in MRI, for pulses described as being 90 degree ($\pi/2$) or 180 degree ($\pi$) pulses, the actual spin rotation angles may not be exactly 90 or 180 degrees, due to variations in physical properties.

What is claimed is:

1. A method of magnetic resonance imaging, comprising:
   generating an inversion pulse to substantially invert magnetic moments of a first component of a sample, the first component having a first $T_2$, and wherein the sample further includes a second component having a second $T_2$ less than the first $T_2$;
   after an inversion time TI, generating an ultra-short TE pulse sequence to selectively excite magnetic moments included in a first slice of the sample; and
   detecting a generated signal based on the selective excitation of the magnetic moments in the first slice of the sample, and wherein TI is selected to reduce a contribution to the generated signal from magnetic moments of the first component with respect to the second component.

2. A method of magnetic resonance imaging, comprising:
   generating a fat suppression pulse to excite magnetic moments of a fat component of a sample, wherein the sample further includes a first component having a first $T_2$ and a second component having a second $T_2$ less than the first $T_2$;
   generating a 90 degree pulse to rotate magnetic moments of a first component of the sample having a first $T_2$ 90 degrees;
   generating a dephasing gradient pulse to de-phase magnetic moments of the first component of the sample;
   generating an ultra-short TE pulse sequence to selectively excite magnetic moments included in the first slice of the sample; and
   detecting a generated signal based on the selective excitation of the magnetic moments in the first slice of the sample.

3. The method of claim 1, wherein the first component has a first $T_1$, and wherein TI is selected based on $T_1$.

4. The method of claim 1 or 2, wherein generating the ultra-short TE pulse sequence comprises:
   generating an excitation RF pulse and a slice selection gradient pulse to selectively excite the magnetic moments included in the first slice of the sample, the slice selection gradient pulse in a first direction; and
   subsequently reversing the slice selection gradient pulse from the first direction to a second, opposite direction to selectively excite the magnetic moments included in the first slice of the sample.

5. The method of claim 1 or 2, wherein the first slice has a thickness of about 4 mm to about 8 mm.

6. The method of claim 1 or 2, wherein the first slice has a thickness of about 2 mm to about 4 mm.

7. The method of claim 1 or 2, wherein the first slice has a thickness of about 2 mm or less.

8. The method of claim 1 or 2, further comprising:
   generating a fat suppression pulse prior to generating the ultra-short TE pulse sequence.

9. The method of claim 1 or 2, further comprising:
   generating data indicative of the generated signal.

10. The method of claim 9, further comprising:
    generating an echo pulse sequence to selectively excite magnetic moments included in the first slice of the sample subsequent to generating the ultra-short TE pulse sequence to selectively excite magnetic moments included in the first slice of the sample; and
    detecting a generated echo signal based on the selective excitation of the magnetic moments included in the first slice of the sample with the echo pulse sequence.

11. The method of claim 10, wherein the echo pulse sequence is selected from a gradient echo pulse sequence and a spin echo pulse sequence.

12. The method of claim 10, further comprising:
    generating echo data indicative of the generated echo signal based on the echo pulse sequence; and
    subtracting the echo data from the data.

13. The method of claim 10, further comprising:
    generating another echo pulse sequence to selectively excite magnetic moments included in the first slice of the sample subsequent to generating the echo pulse sequence; and
    detecting another generated echo signal based on the selective excitation of the magnetic moments included in the first slice of the sample with the another echo pulse sequence.

14. The method of claim 1 or 2, wherein the ultra-short TE pulse sequence is characterized by an echo time TE, and wherein TE is about 80 microseconds or less.

15. The method of claim 1 or 2, further comprising:
    determining the second $T_2$ based on the generated signal.

16. The method of claim 1 or 2, wherein the first $T_2$ is 10 ms or greater.

17. The method of claim 1 or 2, wherein the second $T_2$ is less than 10 ms.

18. The method of claim 1 or 2, wherein the second $T_2$ is between about 0.05 and about 0.5 ms.

19. The method of claim 1 or 2, further comprising:
    generating image data based on the detecting of the generated signal; and
    generating an image based on the image data.

20. The method of claim 19, wherein the sample includes tissue.

21. The method of claim 20, further comprising:
    incorporating one or more contrast agents in the tissue prior to generating image data.

22. The method of claim 21, wherein the one or more contrast agents include a gadolinium chelate.

23. The method of claim 19, further comprising implementing anti-aliasing techniques to reduce artifacts in the generated image.

24. The method of claim 19, further comprising implementing random sampling techniques to reduce artifacts in the generated image.

25. The method of claim 19, further comprising:
generating the image using multi-slice imaging techniques, wherein slices of the multi-slice imaging are selected using different resonance frequency offsets.

26. The method of claim 1, further comprising:
generating the inversion pulse at a time based on at least one of a breath hold gate signal and a cardiac gate signal.

27. The method of claim 1, wherein the magnetic moments comprise proton magnetic moments.

28. The method of claim 1, wherein the magnetic moments comprise nuclei magnetic moments.

29. The method of claim 28, wherein the nuclei are selected from the group consisting of sodium and phosphorus.

30. An article comprising one or more machine-readable storage media having stored thereon instructions that, when executed by one or more machines, results in activities comprising:
generating an inversion pulse to substantially invert magnetic moments of a first component of a sample, the first component having a first $T_2$, and wherein the sample further includes a second component having a second $T_2$ less than the first $T_2$;
after an inversion time TI, generating an ultra-short TB pulse sequence to selectively excite magnetic moments included in a first slice of the sample; and
detecting a generated signal based on the selective excitation of the magnetic moments in the first slice of the sample, and wherein TI is selected to reduce a contribution to the generated signal from magnetic moments of the first component with respect to the second component.

31. An article comprising one or more machine-readable storage media having stored thereon instructions that, when executed by one or more machines, results in activities comprising:
generating a fat suppression pulse to excite magnetic moments of a fat component of a sample, wherein the sample further includes a first component having a first $T_2$ and a second component having a second $T_2$ less than the first $T_2$;
generating a 90 degree pulse to rotate magnetic moments of a first component of the sample having a first $T_2$ 90 degrees;
generating a dephasing gradient pulse to de-phase magnetic moments of the first component of the sample;
generating an ultra-short TE pulse sequence to selectively excite magnetic moments included in the first slice of the sample; and
detecting a generated signal based on the selective excitation of the magnetic moments in the first slice of the sample.

32. An apparatus for magnetic imaging, comprising:
a magnet to generate an RF field having a magnitude of 30 microTesla or greater;
a magnet controller in communication with the magnet, the magnet controller configured to cause the magnet to:
generate an excitation RF pulse and a slice selection gradient pulse, the slice selection gradient pulse in a first direction, the slice selection gradient pulse having a gradient slew rate and a gradient strength; and
subsequently reverse the slice selection gradient pulse from the first direction to a second, opposite direction, wherein the gradient slew rate is 200 T/m or faster.

33. The apparatus of claim 32, wherein the gradient strength is 50 T/m or more.

34. An apparatus for magnetic imaging comprising:
a magnet to generate an RF field having a magnitude of 30 microTesla or greater;
a magnet controller in communication with the magnet, the magnet controller configured to cause the magnet to:
generate an excitation RE pulse and a slice selection gradient pulse, the slice selection gradient pulse in a first direction, the slice selection gradient pulse having a gradient slew rate and a gradient strength; and
subseguently reverse the slice selection gradient pulse from the first direction to a second, opposite direction, wherein the gradient strength is 50 T/m or more.

* * * * *

UNITED STATES PATENT AND TRADEMARK OFFICE
CERTIFICATE OF CORRECTION

PATENT NO. : 7,474,097 B2
APPLICATION NO. : 10/571039
DATED : January 6, 2009
INVENTOR(S) : Mark Bydder et al.

Page 1 of 1

It is certified that error appears in the above-identified patent and that said Letters Patent is hereby corrected as shown below:

ON THE TITLE PAGE

Item [56] (Other Publications), delete "1991: 179:" and insert --1991; 179:--;

IN THE CLAIMS:

Column 25, line 31 (Claim 30), delete "TB" and insert --TE--;

Column 26, line 7 (Claim 31), delete "a first $T_290$" and insert --a first $T_2$ 90--;

Column 26, line 31 (Claim 34), delete "imaging comprising" and insert --imaging, comprising--;

Column 26, line 36 (Claim 34), delete "RE" and insert --RF--;

Column 26, line 40 (Claim 34), delete "subseguently" and insert --subsequently--.

Signed and Sealed this

Thirty-first Day of March, 2009

JOHN DOLL
*Acting Director of the United States Patent and Trademark Office*